(12) United States Patent
Stephens et al.

(10) Patent No.: US 6,403,306 B1
(45) Date of Patent: Jun. 11, 2002

(54) SEROGROUP-SPECIFIC NUCLEOTIDE SEQUENCES IN THE MOLECULAR TYPING OF BACTERIAL ISOLATES AND THE PREPARATION OF VACCINES THERETO

(75) Inventors: David S. Stephens, Stone Mountain, GA (US); John S. Swartley, Westport, CT (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 08/936,107

(22) Filed: Sep. 23, 1997

Related U.S. Application Data

(60) Provisional application No. 60/069,885, filed on Apr. 9, 1997.

(51) Int. Cl.$^7$ ................................................. C12Q 1/68
(52) U.S. Cl. ..................... 435/6; 536/23.7; 536/24.3; 536/24.32; 435/320.1; 435/975
(58) Field of Search ............................. 536/23.1, 23.7, 536/24.3, 24.32; 435/6, 975, 69.1, 69.3, 172.1, 172.3, 320.1

(56) References Cited

PUBLICATIONS

Swartley et al. Proc. Natl. Acad. Sci. USA. Jan. 1997. 94: 271–276.*
Devereux, J. et al., "A comprehensive set of sequence analysis programs for the VAX," (*1984*) *Nucleic Acids Research*, 12(1):387–395.
Edupuganti, S. et al., "Expression of Capsular Polysaccharide in *Neisseria Meningitidis*: Comparison of Biosynthetic and Transport Genetic Loci Responsible for Serogroup A, B, C, Y and W–135 Capsules," (1996), Poster, Biomedicine '96, Washington, D.C.
Edupuganti, S. et al., "Expression of Capsular Polysaccharide in *Neisseria Meningitidis*: Comparison of Biosynthetic and Transport Genetic Loci Responsible for Serogroup A, B, C, Y and W–135 Capsules," (1996), Poster, 10th International Pathogenic Neisseria Conference, Sep. 8–13, 1996, Baltimore, Maryland USA.
Edwards, U et al., "Molecular analysis of the biosynthesis pathway of the α–2,8 polysialic acid capsule by *Neisseria meningitidis* serogroup B," (1994) *Molecular Microbiology* 14(1):141–149.
Feavers, I.M. et al., "Molecular Analysis of the Serotyping Antigens of *Neisseria meningitidis*," (1992) *Infection and Immunity* 60(9):3620–3629.
Frosch, M. et al., "Conserved Outer Membrane Protein of *Neisseria meningitidis* Involved in Capsule Expression," (1992) *Infection and Immunity* 60(3):798–803.
Frosch, M. et al., "Evidence for a common molecular origin of the capsule gene loci in Gram–negative bacteria expression group II capsular polysaccharides," (1991) *Molecular Microbiology* 5(5):1251–1263.

Ganguli, S. et al., "Molecular Cloning and Analysis of Genes for Sialic Acid Synthesis in *Neisseria meningitidis* Group B and Purification of the Meningococcal CMP–NeuNAc Synthetase Enzyme," (1994) *J. Bacteriology* 176(15):4583–4589.
Hammerschmidt, S. et al., "Modulation of cell surface sialic acid expression in *Neisseria meningitidis* via a transposable genetic element," (1996) *The EMBO Journal* 15(1):192–198.
Marfin, A.A. et al., "Evidence for switching of ET5 Capsular group B *Neisseria meningitidis* to capsular group C during an outbreak of meningococcal disease in Oregon," Poster, Presented at the 36th Annual International Conference on Antimicrobial agents and Chemotherapy (ICAAC), Sep. 16–21, 1996, New Orleans, LA, USA.
McAllister, C.F. and Stephens, D.S., "Analysis in *Neisseria meningitidis* and other Neisseria species of genes homologous to the FKBP immunophilin family," (1993) *Molecular Microbiology* 10(1):13–23.
Swartley, J.S. et al., "Expression of Sialic Acid and Polysialic Acid in Serogroup B *Neisseria meningitidis*: Divergent Transcription of Biosynthesis and Transport Operons through a Common Promoter Region," (1996) *J. Bacteriology* 178(14):4052–4059.
Swartley, J.S. and Stephens, D.S., "Identification of a Genetic Locus Involved in the Biosynthesis of N–Acetyl–D– Mannosamine, a Precursor of the (α2→8)–Linked Polysialic Acid Capsule of Serogroup B *Neisseria meningitidis*," (1994) *J. Bacteriology* 176(5):1530–1534.
Zhou, D. et al., "Lipooligosaccharide Biosynthesis in Pathogenic Neisseria," (1994) *J. Biological Chemistry* 269(15):11162–11169.
Zhou, Jiaji and Spratt, B.G., "Sequence diversity within the argF, fbp and recA genes of natural isolates of *Neisseria meningitidis*: interspecies recombination within the argF gene," (1992) *Molecular Microbiology* 6(15):2135–2146.

\* cited by examiner

*Primary Examiner*—Jennifer E. Graser
(74) *Attorney, Agent, or Firm*—Greenlee Winner and Sullivan, PC

(57) ABSTRACT

The present invention is based on the discovery of meningococcal isolates having genetic markers of a particular serogroup but expressing a capsular polysaccharide of a different serogroup. These isolates and prototype serogroup A, B, C, Y and W-135 strains were used to define the capsular biosynthetic operon of the major meningococcal serogroups and to show that capsule switching occurs as a result of allelic exchange of, for example, the polysialyltransferase gene. Findings of capsule switching in vivo indicate that closely related virulent meningococcal clones may not be recognized by traditional serogroup-based surveillance and can escape vaccine-induced or natural protective immunity by capsule switching. The invention provides recombinant meningococcal strains, recombinant DNA constructs and immunological preparations useful as diagnostic probes for detection and diagnosis of meningococcal diseases, screening for specific meningococcal serogroups and broad based immunizations with multivalent capsular polysaccharide conjugate vaccines.

7 Claims, 22 Drawing Sheets

FIG. 2

|  |  | 1 | | | | | 70 |
|---|---|---|---|---|---|---|---|
| NMB | synC-D | GTCCGGAGAT | AACCTATGGG | TTAAACGCCCC | AGGCAATGGA | GACTTCAGCG | TCAACGAATA | TGAAACATTA |
| B301#1 | synC-D | GTCCGGAGAT | AACCTATGGG | TTAAACGCCCC | AGGCAATGGA | GACTTCAGCG | TCAACGAATA | TGAAACATTA |
| C301#1 | synC-E | GTCCGGAGAT | AACCTATGGG | TTAAACGCCCC | AGGCAATGGA | GACTTCAGCG | TCAACGAATA | TGAAACATTA |
| FAM18 | synC-E | GTCCGGAGAT | AACCTATGGG | TTAAACGCCCC | AGGCAATGGA | GACTTCAGCG | TCAACGAATA | TGAAACATTA |
| Consensus |  | GTCCGGAGAT | AACCTATGGG | TTAAACGCCCC | AGGCAATGGA | GACTTCAGCG | TCAACGAATA | TGAAACATTA |

|  |  | 71 | | | | | 140 |
|---|---|---|---|---|---|---|---|
| NMB | synC-D | TTTGGTAAGG | TCGCTGCTTG | CAATATTCGC | AAAGGTGCTC | AAATCAAAAA | AACTGATATT | GAATAAtgcT |
| B301#1 | synC-D | TTTGGTAAGG | TCGCTGCTTG | CAATATTCGC | AAAGGTGCTC | AAATCAAAAA | AACTGATATT | GAATAAtgcT |
| C301#1 | synC-E | TTTGGTAAaa | TtgCTGCTTG | tgATATTCGC | AAAGGTGCTC | AAATCAAAAA | AACTGATATc | GAATAAaaaT |
| FAM18 | synC-E | TTTGGTAAGG | TCGCTGCTTG | CAATATTCGC | AAAGGTGCTC | AAATCAAAAA | AACTGATATT | GAATAAaaaT |
| Consensus |  | TTTGGTAAGG | TCGCTGCTTG | CAATATTCGC | AAAGGTGCTC | AAATCAAAAA | AACTGATATT | GAATAA---T | synC

|  |  | 141 | | | | | 210 |
|---|---|---|---|---|---|---|---|
| NMB | synC-D | .TATtAAcTt | AgTtAcTTTA | tTaAcAgagG | attGgCTaTT | ACATAtAGct | aATTcTCATT | AAtttTtaAg |
| B301#1 | synC-D | .TATtAAcTt | AgTtAcTTTA | tTaAcAgagG | attGgCTaTT | ACATAtAGct | aATTcTCATT | AAtttTtaAg |
| C301#1 | synC-E | CTATaAAtTg | AcTcAaTTTA | aTgAtAatcG | gcTGacTtTT | ......cAGtc | gATTaTCATT | AAaaaTaTAc |
| FAM18 | synC-E | CTATaAAtTg | AcTcAaTTTA | aTgAtAatcG | gcTGacTtTT | ......cAGtc | gATTaTCATT | AAaaaTaTAc |
| Consensus |  | -TAT-AA-T- | A-T-A-TTTA | -T-A-A---G | --TG-CT-TT | ------AG-- | -ATT-TCATT | AA---T--A- | synC

|  |  | 211 | | | | | 280 |
|---|---|---|---|---|---|---|---|
| NMB | synC-D | aGAtAcAatA | ATGCTaaAGA | AAATAAaAAA | AGCTCTtTTt | CAgCCtAAAA | AgTtTTtTcA | AGATTCaatG |
| B301#1 | synC-D | aGAtAcAatA | ATGCTaaAGA | AAATAAaAAA | AGCTCTtTTt | CAgCCtAAAA | AgTtTTtTcA | AGATTCaatG |
| C301#1 | synC-E | gGAaAaAcaA | ATGtTgcAGA | AAATAAgAAA | AGCTCTcTTc | CAcCCaAAAA | AaTTCTTcCA | AGATTCccaG |
| FAM18 | synC-E | gGAaAaAcaA | ATGtTgcAGA | AAATAAgAAA | AGCTCTcTTc | CAcCCaAAAA | AaTTCTTcCA | AGATTCccaG |
| Consensus |  | -GA-A-A--A | ATG-T--AGA | AAATAA-AAA | AGCTCT-TT- | CA-CC-AAAA | A-TT-TT-CA | AGATTC---G |

SynD/E

B301 #1   (B)   ctrA-synX    A CAT........ CAGGCA
B301 #2   (B)   ctrA-synX    - ----------- ------
C301 #1   (C)   ctrA-synX    - ----------- TGAATG
C301 #2   (C)   ctrA-synX    - ----------- TGAATG
C301 #3   (C)   ctrA-synX    - ----------- TGAATG
NMB       (B)   ctrA-synX    - ---TACTTATA ---ATG
FAM18     (C)   ctrA-synX    - ---TACTTATA ---ATG
GA0929    (Y)   ctrA-synX    - ---TACTTATA ---ATG
GA1002    (W)   ctrA-synX    G ---TACTTATA ---ATG
6083      (W)   ctrA-synX    - -GC-------- ---ATG
```

B301 #1    (B)    fkbp  ACCCGCCGTCAACCACCCGAGGACCTGAGCCACGCCC
B301 #2    (B)    fkbp  ------------------------------------
C301 #1    (C)    fkbp  ------------------------------------
C301 #2    (C)    fkbp  ------------------------------------
C301 #3    (C)    fkbp  ------------------------------------
GA0929     (Y)    fkbp  ---------------------G--------------
F8239      (A)    fkbp  --------C-------A-------------------
GA1002     (W)    fkbp  ----------------A------------G---T-
6083       (W)    fkbp  C-------C--------A-G------------C---
NMB        (B)    fkbp  C-------C--------A-G------------C---
M986       (B)    fkbp  C-------C--------A-G------------C---
2996       (B)    fkbp  C-------C--------A-G------------C---
C114       (B)    fkbp  C-------C--------A-G------------.---
KB         (B)    fkbp  T-------C--------A--A-----T-CT--TC---
269B       (B)    fkbp  T-------C--------A--A-----T-CT--TC---
FAM18      (C)    fkbp  T-------C--------A--A-----T-CT--TC---

N. ciner.         fkbp  --A-A--AC---T--T-------------T--TC---
N. lact.          fkbp  T--------------T-----A----TGCT--TCT--
N. poly.          fkbp  -T-------------T-A--------T-CTT-TCT--
N. elong.         fkbp  T--TA--TC-C-GT-T--A-----T-C-----TC-T-
N. sicca          fkbp  C-TT-GT-CGTG-TC-T------T-G-----G-----
N. flav.          fkbp  T--TA--TC-C-GT-T--A-----T-C-----TC-T-
N. subfl.         fkbp  T--TA--TC-C-GT-T--A-----T-C---A-TA-TT
```

B301 #1    (B)   recA   CTCACCCCCCCCGCCACTGACTCCCGGGTAGGGGC
B301 #2    (B)   recA   -----------------------------------
C301 #1    (C)   recA   -----------------------------------
C301 #2    (C)   recA   -----------------------------------
C301 #3    (C)   recA   -----------------------------------
Nm-HF46    (A)   recA   -----------------------------------
NMB        (B)   recA   -----------------------------------
Nm-44/76   (B)   recA   -----------------------------------
FAM18      (C)   recA   -----------------------------------
Nm-N94II   (Y)   recA   ---------------------------ACCGCC---
F8239      (A)   recA   ---C-------T---------------ACCGCC---
Nm-S3446   (B)   recA   ---C-------T---------------ACCGCC---
Nm-HF130   (B)   recA   ---C-------T-T----A---T---ACC-CC---
Ng-FA19          recA   -C-C-A---------G-----CT-TA--C-CC---
Nm-M470    (B)   recA   ---C--------C-----A---TT--ACCGCC--T
GA0929     (Y)   recA   ---C--------C-----A---TT--ACCGCC--T
GA1002     (W)   recA   AC-C-A-----T------A---T---ACC-CC-A-
Nm-HF116   (Z)   recA   AC-C-A-----T------A---T---ACC-CCA--
Nm-P63     (B)   recA   A-TCTATATGA-C-TGGCCGTC-T--ACC-CC-A-
```

FIG. 3B-3

```
AATACATCACCAATATTTAGCGTACCGGTAGAAGCATAACCATCGCCAAACTGGGTAAAA
GACTGATTCACCTGAGCTTTATACAAGACTGCGCTACAGCATGATTGACGTCAATCAAC
TCTACTTCAGGAATTTGAGCTTCAGACTGTTGCCCCAATGAGACAACTTTTTTTGCACTT
GGGCCAGAGGAGGGAATAGCACTACATGCACTTCCCAAAATTAAAAAAGAAATTACAATA
CAAAACTTTAACTTAAGCATAAAATAAAAAATCTCATTAAGTATGATTGTTTTTAAATAA
ATTTAAAACCTACCAGAGATACAATACCACTTTATTTTGTAGAACACAAACGTGTATAAT
ATATGACATAAACATCATCTTCGAAATAATATTGGGGCTTAGGAAGCAAAATCATCAAAA
AACGTGATAAGCTCCTAATATTTTTAACACATTACTATATTACACATAGGATATTCCAAT
GAAAGTCTTAACCGTCTTTGGCACTCGCCCTGAAGCTATTAAAATGGCGCCTGTAATTCT
AGAGTTACAAAAACATAACACAATTACTTCAAAAGTTTGCATTACTGCACAGCATCGTGA
AATGCTAGATCAGGTTTTGAGCCTATTCGAAATCAAAGCTGATTATGATTTAAATATCAT
GAAACCCAACCAGAGCCTACAAGAAATCACAACAAATATCATCTCAAGCCTTACCGATGT
TCTTGAAGATTTCAAACCTGACTGCGTCCTTGCTCACGGAGACACCACAACAACTTTTGC
AGCTAGCCTTGCTGCATTCTATCAAAAAATACCTGTTGGCCACATTGAAGCAGGCCTGAG
AACTTATAATTTATACTCTCCTTGGCCAGAGGAAGCAAATAGGCGTTTAACAAGCGTTCT
AAGCCAGTGGCATTTTGCACCTACTGAAGATTCTAAAAATAACTTACTATCTGAATCAAT
ACCTTCTGACAAAGTTATTGTTACTGGAAATACTGTCATAGATGCACTAATGGTATCTCT
AGAAAAACTAAAAATAACTACAATTAAAAACAAATGGAACAAGCTTTTCCATTTATTCA
GGACAACTCTAAAGTAATTTTAATTACCGCTCATAGAAGAGAAATCATGGGGAAGGTAT
TAAAAATATTGGACTTTCTATCTTAGAATTAGCTAAAAAATACCCAACATTCTCTTTTGT
GATTCCGCTCCATTTAAATCCTAACGTTAGAAAACCAATTCAAGATTTATTATCCTCTGT
GCACAATGTTCATCTTATTGAGCCACAAGAATACTTACCATTCGTATATTTAATGTCTAA
AAGCCATATAATATTAAGTGATTCAGGCGGCATACAAGAAGAAGCTCCATCCCTAGGAAA
ACCAGTTCTTGTATTAAGAGATACTACAGAACGTCCTGAAGCTGTAGCTGCAGGAACTGT
AAAATTAGTAGGTTCTGAAACTCAAAATATTATTGAGAGCTTTACACAACTAATTGAATA
CCCTGAATATTATGAAAAAATGGCTAATATTGAAAACCCTTACGGGATAGGTAATGCCTC
AAAAATCATTGTAGAAACTTTATTAAAGAATAGATAAAATGTTTATACTTAATAACAGAA
AATGGCGTAAACTTAAAAGAGACCCTAGCGCTTTCTTTCGAGATAGTAAATTTAACTTTT
TAAGATATTTTTCTGCTAAAAAATTTGCAAAGAATTTTAAAAATTCATCACATATCCATA
AAACTAATATAAGTAAAGCTCAATCAAATATTTCTTCAACCTTAAAAGAAAATCGGAAAC
AAGATATGTTAATTCCTATTAATTTTTTTAATTTTGAATATATAGTTAAAAAACTTAACA
ATCAAAACGCAATAGGTGTATATATTCTTCCTTCTAATCTTACTCTTAAGCCTGCATTAT
GTATTCTAGAATCACATAAAGAAGACTTTTTAAATAAATTTCTTCTTACTATTTCCTCTG
AAAATTTAAAGCTTCAATACAAATTTAATGGACAAATAAAAAATCCTAAGTCCGTAAATG
AAATTTGGACAGATTTATTTAGCATTGCTCATGTTGACATGAAACTCAGCACAGATAGAA
CTTTAAGTTCATCTATATCTCAATTTTGGTTCAGATTAGAGTTCTGTAAAGAAGATAAGG
ATTTTATCTTATTTTCTACAGCTAACAGATATTCTAGAAAACTTTGGAAGCACTCTATTA
AAAATAATCAATTATTTAAAGAAGGCATACGAAACTATTCAGAAATATCTTCATTACCCT
ATGAAGAAGATCATAATTTTGATATTGATTTAGTATTTACTTGGGTCAACTCAGAAGATA
AGAATTGGCAAGAGTTATATAAAAAATATAAGCCCGACTTTAATAGCGATGCAACCAGTA
CATCAAGATTCCTTAGTAGAGATGAATTAAAATTCGCATTACGCTCTTGGGAAATGAGTG
GATCCTTCATTCGAAAAATTTTTATTGTCTCTAATTGTGCTCCCCCAGCATGGCTAGATT
TAAATAACCCTAAAATTCAATGGGTATATCACGAAGAAATTATGCCACAAAGTGCCCTTC
CTACTTTTAGCTCACATGCTATTGAAACCAGCTTGCACCATATACCAGGAATTAGTAACT
ATTTTATTTACAGCAATGACGACTTCCTATTAACTAAACCATTGAATAAAGACAATTTCT
TCTATTCGAATGGTATTGCAAAGTTAAGATTAGAAGCATGGGGAAATGTTAATGGTGAAT
GTACTGAAGGAGAACCTGACTACTTAAATGGTGCTCGCAATGCGAACACTCTCTTAGAAA
```

FIG. 4A

```
AGGAATTTAAAAAATTTACTACTAAACTACATACTCACTCCCCTCAATCCATGAGAACTG
ATATTTTATTTGAGATGGAAAAAAAATATCCAGAAGAGTTTAATAGAACACTACATAATA
AATTCCGATCTTTAGATGATATTGCAGTAACGGGCTATCTCTATCATCATTATGCCCTAC
TCTCTGGACGAGCACTACAAAGTTCTGACAAGACGGAACTTGTACAGCAAAATCATGATT
TCAAAAAGAAACTAAATAATGTAGTGACCTTAACTAAAGAAAGGAATTTTGACAAACTTC
CTTTGAGCGTATGTATCAACGATGGTGCTGATAGTCACTTGAATGAAGAATGGAATGTTC
AAGTTATTAAGTTCTTAGAAACTCTTTTCCCATTACCATCATCATTTGAGAAATAAGTTA
AATTATGAAGAACCTTTGAGTGCAATTCGAAGGTTCTTCATTCATATTATTCATATTTTG
GAGAAATTATGTTATCTAATTTAAAAACAGGAAATAATATCTTAGGATTACCTGAATTTG
AGTTGAATGGCTGCCGATTCTTATATAAAAAGGTATAGAAAAACAATTATTACTTTTT
CAGCATTTCCTCCTAAAGATATTGCTCAAAAATATAATTATATAAAAGATTTTTTAAGTT
CTAATTATACTTTTTTAGCATTCTTAGATACCAAATATCCAGAAGATGATGCTAGAGGCA
CTTATTACATTACTAATGAGTTAGATAATGGATATTTACAAACCATACATTGTATTATTC
AATTATTATCGAATACAAATCAAGAAGATACCTACCTTTTGGGTTCAAGTAAAGGTGGCG
TTGGCGCACTTCTACTCGGTCTTACATATAATTATCCTAATATAATTATTAATGCTCCTC
AAGCCAAATTAGCAGATTATATCAAAACACGCTCGAAACCATTCTTTCATATATGCTTG
GAACCTCTAAAAGATTTCAAGATATTAATTACGATTATATCAATGACTTCTTACTATCTA
AAATTAAGACTTGCGACTCCTCACTTAAATGGAATATTCATATAACTTGCGGAAAAGATG
ATTCATATCATTTAAATGAATTAGAAATTCTAAAAAATGAATTTAATATAAAAGCTATTA
CGATTAAAACCAAACTAATTTCTGGCGGGCATGATAATGAAGCAATTGCCCACTATAGAG
AATACTTTAAAACCATAATCCAAAATATATAAAATGCGTAAGATTACTTTTATTATCCCT
ATAAAACAGTCTTTAATAAAACCTGATTGCTTTATACGCCTCTTTTTTAATTTATTTTTG
CTAAAAAAATTCTCAAGTAAATACGGATTTTCTATATTAGTTGCAGACAACAGTAACTTC
CTTTGGAAAAATATTATTAAATTAATTACAAAATTTTACAAATGTAATTATATTAGTATT
AAATCTCATAATACTTTTTATACGCCTGCTAAAATTAAAAATGCAGCTGCCATCTATAGT
TTTAATACCTTGAATTCAAATTACATTTTATTCTTAGATGTTGACGTTTTATTATCGGAA
AATTTTATCCAACATTTAATAAAAAAAACAAAAACCAATATCGCCTTTGATTGGTACCCT
GTTTCATTCTTAAACAAACAATTTGGGATTATAAATTTTATATTATTCTCATATAAAGGT
AATCTAAATATAGAAGAATCATTCATTATACAAACAGGGTTTGTAACTGGCTTACAATTA
TTTAATTCTGATTTTTTCTACAAAACAGCTGGATACAATGAAAGCTTTCTTGGCTATGGC
TGTGAAGATATTGAAATGATTCACAGAGCAACATTATTATTAAATATTAGACCTGCCTTT
AATGAAAATCATCAATATTTTACAGATGATAGAGGATATATGCCTTCTAAATTAACCGGA
TTTCGAAATTATTTTTATTATTTGAAAAGAGATGAATTTTCAAACTTACAGATAACTCCT
AAACATTTCTGGCATAAGCGAAAAATAAATCAAATATCTAAAAAATAGATATCAAAAT
GATGTAAAAATGATTCAGATTATGAAAGATTTTGATCGAAATTTCTAAAAAATTAACGA
GCTGTCTTGCCCATATGAATCCTGATTACTTTAATTTAATTATGAAAAATATTCTCGTTA
CCGGCGGCACCGGTTTTATCGGCTCGCACACCGTTGTTTCTTTGCTGAAAAGCGGCCATC
AAGTCGTGATTTTGGATAACCTAT
```

FIG. 4B

| | | | | | | | | | | | | | | |
|---|---|---|---|---|---|---|---|---|---|---|---|---|---|---|
| Met 1 | Lys | Val | Leu | Thr 5 | Val | Phe | Gly | Thr | Arg 10 | Pro | Glu | Ala | Ile | Lys Met 15 |
| Ala | Pro | Val | Ile 20 | Leu | Glu | Leu | Gln | Lys 25 | His | Asn | Thr | Ile | Thr Ser 30 | Lys |
| Val | Cys | Ile 35 | Thr | Ala | Gln | His | Arg 40 | Glu | Met | Leu | Asp | Gln 45 | Val | Leu Ser |
| Leu | Phe 50 | Glu | Ile | Lys | Ala | Asp 55 | Tyr | Asp | Leu | Asn | Ile 60 | Met | Lys | Pro Asn |
| Gln 65 | Ser | Leu | Gln | Glu | Ile 70 | Thr | Thr | Asn | Ile | Ile 75 | Ser | Ser | Leu | Thr Asp 80 |
| Val | Leu | Glu | Asp | Phe 85 | Lys | Pro | Asp | Cys | Val 90 | Leu | Ala | His | Gly | Asp Thr 95 |
| Thr | Thr | Thr | Phe 100 | Ala | Ala | Ser | Leu | Ala 105 | Ala | Phe | Tyr | Gln | Lys 110 | Ile Pro |
| Val | Gly | His 115 | Ile | Glu | Ala | Gly | Leu 120 | Arg | Thr | Tyr | Asn | Leu 125 | Tyr | Ser Pro |
| Trp | Pro 130 | Glu | Glu | Ala | Asn | Arg 135 | Arg | Leu | Thr | Ser | Val 140 | Leu | Ser | Gln Trp |
| His 145 | Phe | Ala | Pro | Thr | Glu 150 | Asp | Ser | Lys | Asn | Asn 155 | Leu | Leu | Ser | Glu Ser 160 |
| Ile | Pro | Ser | Asp | Lys 165 | Val | Ile | Val | Thr | Gly 170 | Asn | Thr | Val | Ile | Asp Ala 175 |
| Leu | Met | Val | Ser 180 | Leu | Glu | Lys | Leu | Lys 185 | Ile | Thr | Thr | Ile | Lys 190 | Lys Gln |
| Met | Glu | Gln 195 | Ala | Phe | Pro | Phe | Ile 200 | Gln | Asp | Asn | Ser | Lys 205 | Val | Ile Leu |
| Ile | Thr | Ala 210 | His | Arg | Arg | Glu | Asn 215 | His | Gly | Glu | Gly | Ile 220 | Lys | Asn Ile |
| Gly 225 | Leu | Ser | Ile | Leu | Glu 230 | Leu | Ala | Lys | Lys | Tyr 235 | Pro | Thr | Phe | Ser Phe 240 |
| Val | Ile | Pro | Leu | His 245 | Leu | Asn | Pro | Asn | Val 250 | Arg | Lys | Pro | Ile | Gln Asp 255 |
| Leu | Leu | Ser | Ser 260 | Val | His | Asn | Val | His 265 | Leu | Ile | Glu | Pro | Gln 270 | Glu Tyr |

FIG. 5A

```
Leu Pro Phe Val Tyr Leu Met Ser Lys Ser His Ile Ile Leu Ser Asp
        275             280             285

Ser Gly Gly Ile Gln Glu Glu Ala Pro Ser Leu Gly Lys Pro Val Leu
    290             295             300

Val Leu Arg Asp Thr Thr Glu Arg Pro Glu Ala Val Ala Ala Gly Thr
305             310             315             320

Val Lys Leu Val Gly Ser Glu Thr Gln Asn Ile Ile Glu Ser Phe Thr
            325             330             335

Gln Leu Ile Glu Tyr Pro Glu Tyr Tyr Glu Lys Met Ala Asn Ile Glu
        340             345             350

Asn Pro Tyr Gly Ile Gly Asn Ala Ser Lys Ile Ile Val Glu Thr Leu
        355             360             365

Leu Lys Asn Arg *
    370
```

FIG. 5B

| | | | | | | | | | | | | | | |
|---|---|---|---|---|---|---|---|---|---|---|---|---|---|---|
|Met|Phe|Ile|Leu|Asn|Asn|Arg|Lys|Trp|Arg|Lys|Leu|Lys|Arg|Asp|Pro|
|1| | | |5| | | |10| | | |15| | |

Met Phe Ile Leu Asn Asn Arg Lys Trp Arg Lys Leu Lys Arg Asp Pro
 1               5               10              15

Ser Ala Phe Phe Arg Asp Ser Lys Phe Asn Phe Leu Arg Tyr Phe Ser
         20              25              30

Ala Lys Lys Phe Ala Lys Asn Phe Lys Asn Ser Ser His Ile His Lys
         35              40              45

Thr Asn Ile Ser Lys Ala Gln Ser Asn Ile Ser Ser Thr Leu Lys Glu
 50              55              60

Asn Arg Lys Gln Asp Met Leu Ile Pro Ile Asn Phe Phe Asn Phe Glu
 65              70              75              80

Tyr Ile Val Lys Lys Leu Asn Asn Gln Asn Ala Ile Gly Val Tyr Ile
             85              90              95

Leu Pro Ser Asn Leu Thr Leu Lys Pro Ala Leu Cys Ile Leu Glu Ser
            100             105             110

His Lys Glu Asp Phe Leu Asn Lys Phe Leu Leu Thr Ile Ser Ser Glu
            115             120             125

Asn Leu Lys Leu Gln Tyr Lys Phe Asn Gly Gln Ile Lys Asn Pro Lys
 130                135             140

Ser Val Asn Glu Ile Trp Thr Asp Leu Phe Ser Ile Ala His Val Asp
145             150             155             160

Met Lys Leu Ser Thr Asp Arg Thr Leu Ser Ser Ser Ile Ser Gln Phe
                165             170             175

Trp Phe Arg Leu Glu Phe Cys Lys Glu Asp Lys Asp Phe Ile Leu Phe
            180             185             190

Ser Thr Ala Asn Arg Tyr Ser Arg Lys Leu Trp Lys His Ser Ile Lys
    195             200             205

Asn Asn Gln Leu Phe Lys Glu Gly Ile Arg Asn Tyr Ser Glu Ile Ser
210             215             220

Ser Leu Pro Tyr Glu Glu Asp His Asn Phe Asp Ile Asp Leu Val Phe
225             230             235             240

Thr Trp Val Asn Ser Glu Asp Lys Asn Trp Gln Glu Leu Tyr Lys Lys
                245             250             255

Tyr Lys Pro Asp Phe Asn Ser Asp Ala Thr Ser Thr Ser Arg Phe Leu
            260             265             270

Ser Arg Asp Glu Leu Lys Phe Ala Leu Arg Ser Trp Glu Met Ser Gly
    275             280             285

FIG. 6A

```
Ser Phe Ile Arg Lys Ile Phe Ile Val Ser Asn Cys Ala Pro Pro Ala
    290             295             300
Trp Leu Asp Leu Asn Asn Pro Lys Ile Gln Trp Val Tyr His Glu Glu
305             310             315             320
Ile Met Pro Gln Ser Ala Leu Pro Thr Phe Ser Ser His Ala Ile Glu
            325             330             335
Thr Ser Leu His His Ile Pro Gly Ile Ser Asn Tyr Phe Ile Tyr Ser
            340             345             350
Asn Asp Asp Phe Leu Leu Thr Lys Pro Leu Asn Lys Asp Asn Phe Phe
        355             360             365
Tyr Ser Asn Gly Ile Ala Lys Leu Arg Leu Glu Ala Trp Gly Asn Val
    370             375             380
Asn Gly Glu Cys Thr Glu Gly Glu Pro Asp Tyr Leu Asn Gly Ala Arg
385             390             395             400
Asn Ala Asn Thr Leu Leu Glu Lys Glu Phe Lys Lys Phe Thr Thr Lys
            405             410             415
Leu His Thr His Ser Pro Gln Ser Met Arg Thr Asp Ile Leu Phe Glu
            420             425             430
Met Glu Lys Lys Tyr Pro Glu Glu Phe Asn Arg Thr Leu His Asn Lys
        435             440             445
Phe Arg Ser Leu Asp Asp Ile Ala Val Thr Gly Tyr Leu Tyr His His
    450             455             460
Tyr Ala Leu Leu Ser Gly Arg Ala Leu Gln Ser Ser Asp Lys Thr Glu
465             470             475             480
Leu Val Gln Gln Asn His Asp Phe Lys Lys Lys Leu Asn Asn Val Val
            485             490             495
Thr Leu Thr Lys Glu Arg Asn Phe Asp Lys Leu Pro Leu Ser Val Cys
            500             505             510
Ile Asn Asp Gly Ala Asp Ser His Leu Asn Glu Glu Trp Asn Val Gln
        515             520             525
Val Ile Lys Phe Leu Glu Thr Leu Phe Pro Leu Pro Ser Ser Phe Glu
        530             535             540
Lys *
545
```

FIG. 6B

```
Met Leu Ser Asn Leu Lys Thr Gly Asn Asn Ile Leu Gly Leu Pro Glu
 1               5                   10                  15

Phe Glu Leu Asn Gly Cys Arg Phe Leu Tyr Lys Lys Gly Ile Glu Lys
            20                  25                  30

Thr Ile Ile Thr Phe Ser Ala Phe Pro Pro Lys Asp Ile Ala Gln Lys
        35                  40                  45

Tyr Asn Tyr Ile Lys Asp Phe Leu Ser Ser Asn Tyr Thr Phe Leu Ala
    50                  55                  60

Phe Leu Asp Thr Lys Tyr Pro Glu Asp Asp Ala Arg Gly Thr Tyr Tyr
 65                  70                  75                  80

Ile Thr Asn Glu Leu Asp Asn Gly Tyr Leu Gln Thr Ile His Cys Ile
                85                  90                  95

Ile Gln Leu Leu Ser Asn Thr Asn Gln Glu Asp Thr Tyr Leu Leu Gly
            100                 105                 110

Ser Ser Lys Gly Gly Val Gly Ala Leu Leu Leu Gly Leu Thr Tyr Asn
        115                 120                 125

Tyr Pro Asn Ile Ile Ile Asn Ala Pro Gln Ala Lys Leu Ala Asp Tyr
    130                 135                 140

Ile Lys Thr Arg Ser Lys Thr Ile Leu Ser Tyr Met Leu Gly Thr Ser
145                 150                 155                 160

Lys Arg Phe Gln Asp Ile Asn Tyr Asp Tyr Ile Asn Asp Phe Leu Leu
            165                 170                 175

Ser Lys Ile Lys Thr Cys Asp Ser Ser Leu Lys Trp Asn Ile His Ile
            180                 185                 190

Thr Cys Gly Lys Asp Asp Ser Tyr His Leu Asn Glu Leu Glu Ile Leu
        195                 200                 205

Lys Asn Glu Phe Asn Ile Lys Ala Ile Thr Ile Lys Thr Lys Leu Ile
    210                 215                 220

Ser Gly Gly His Asp Asn Glu Ala Ile Ala His Tyr Arg Glu Tyr Phe
225                 230                 235                 240

Lys Thr Ile Ile Gln Asn Ile  *
            245
```

FIG. 7

```
Met Arg Lys Ile Thr Phe Ile Ile Pro Ile Lys Gln Ser Leu Ile Lys
 1               5               10                  15

Pro Asp Cys Phe Ile Arg Leu Phe Phe Asn Leu Phe Leu Leu Lys Lys
             20                  25                  30

Phe Ser Ser Lys Tyr Gly Phe Ser Ile Leu Val Ala Asp Asn Ser Asn
         35                  40                  45

Phe Leu Trp Lys Asn Ile Ile Lys Leu Ile Thr Lys Phe Tyr Lys Cys
     50                  55                  60

Asn Tyr Ile Ser Ile Lys Ser His Asn Thr Phe Tyr Thr Pro Ala Lys
 65                  70                  75                  80

Ile Lys Asn Ala Ala Ala Ile Tyr Ser Phe Asn Thr Leu Asn Ser Asn
                 85                  90                  95

Tyr Ile Leu Phe Leu Asp Val Asp Val Leu Leu Ser Glu Asn Phe Ile
             100                 105                 110

Gln His Leu Ile Lys Lys Thr Lys Thr Asn Ile Ala Phe Asp Trp Tyr
         115                 120                 125

Pro Val Ser Phe Leu Asn Lys Gln Phe Gly Ile Ile Asn Phe Ile Leu
     130                 135                 140

Phe Ser Tyr Lys Gly Asn Leu Asn Ile Glu Glu Ser Phe Ile Ile Gln
145                 150                 155                 160

Thr Gly Phe Val Thr Gly Leu Gln Leu Phe Asn Ser Asp Phe Phe Tyr
             165                 170                 175

Lys Thr Ala Gly Tyr Asn Glu Ser Phe Leu Gly Tyr Gly Cys Glu Asp
             180                 185                 190

Ile Glu Met Ile His Arg Ala Thr Leu Leu Leu Asn Ile Arg Pro Ala
         195                 200                 205

Phe Asn Glu Asn His Gln Tyr Phe Thr Asp Asp Arg Gly Tyr Met Pro
     210                 215                 220

Ser Lys Leu Thr Gly Phe Arg Asn Tyr Phe Tyr Tyr Leu Lys Arg Asp
225                 230                 235                 240

Glu Phe Ser Asn Leu Gln Ile Thr Pro Lys His Phe Trp His Lys Arg
             245                 250                 255

Lys Asn Lys Ser Lys Tyr Leu Lys Asn Arg Tyr Gln Asn Asp Val Lys
             260                 265                 270

Met Ile Gln Ile Met Lys Asp Phe Asp Arg Lys Phe Leu Lys Asn  *
         275                 280                 285
```

FIG. 8

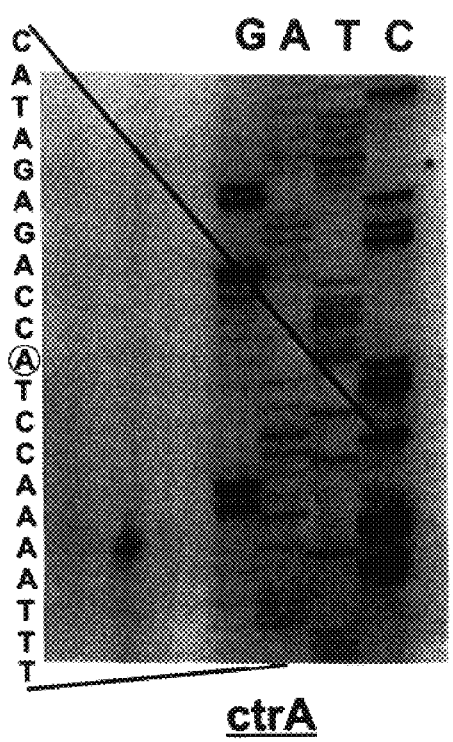 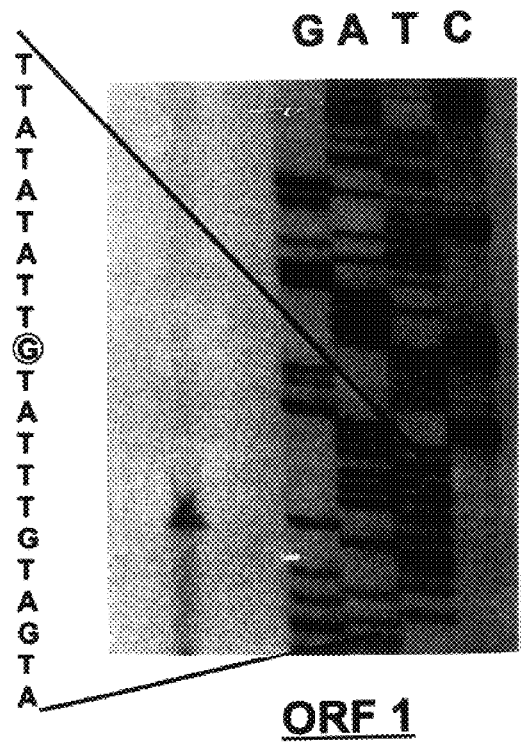
FIG. 13A ctrA
FIG. 13B ORF 1

SEROGROUP-SPECIFIC NUCLEOTIDE SEQUENCES IN THE MOLECULAR TYPING OF BACTERIAL ISOLATES AND THE PREPARATION OF VACCINES THERETO

RELATEDNESS OF THE INVENTION

The subject application is a continuation-in-part of copending U.S. Provisional Application No. 60/069,885, filed on Apr. 9, 1997, which is incorporated herein in its entirety by reference.

This invention was made, at least in part, with funding from the United States National Institute of Allergy and Infectious Diseases, Grant No. AI40247-01. Accordingly, the United States government may have certain rights in this invention.

FIELD OF THE INVENTION

This invention relates generally to the nucleotide sequences of serogroup-specific capsular polysaccharides genes and their use in a method for typing of serogroups of pathogenic bacteria, in particular *Neisseria meningitidis*, and further, relates to capsule gene switching in recombinant strains and the detection thereof.

BACKGROUND OF THE INVENTION

Contagious outbreaks of epidemic diseases constitute public health emergencies requiring rapid treatment and chemoprophylaxis of contacts. Vaccination of the population at risk can be considered if disease cases continue to occur. However, asymptomatic carriage of pathogens in humans is common and some of the adult population may be immunized from previous outbreaks. The factors leading from acquisition of the organism to invasive disease point to a clonal origin of the outbreaks and to an enhanced virulence or altered antigenicity of a particular clone.

*Neisseria meningitidis* is a leading worldwide cause of *meningitis* and rapidly fatal sepsis in otherwise health individuals [Apicella, M. A. (1995) in *Principles and Practice of Infectious Diseases*, eds. Mandell, G. L., Douglas, R. G., and Bennett, J. E., Churchill Livingstone, New York, pp. 1896–1909]. In excess of 350,000 cases of meningococcal disease were estimated to have occurred in 1995 [WHO Report (1996) WHO, Geneva, ISBN 92 4 1561823]. The problem of meningococcal disease is emphasized by the recurrence of major epidemics due to serogroups A, B, and C *N. meningitidis* over the last 20 years, such as: the devastating serogroup A outbreak in sub-Saharan Africa in 1996 [WHO (1996) *Meningitis in Africa. The constant challenge of epidemics.* WHO 21:15 March]; the recent dramatic increases in the incidence of serogroup B and C meningococcal disease in parts of North America [CDC (1995) *MMWR* 44:121–134; Jackson, L. A. et al. (1995) *JAMA* 273:390–394; Wahlen, C. M. et al. (1995) *JAMA* 273:383–389]; and the emergence in Europe and elsewhere of meningococci with decreased susceptibility to antibiotics [Campos, J. et al. (1992) *J. Infect. Dis.* 166:173–177].

Differences in capsular polysaccharide chemical structure determine the meningococcal serogroups [Liu, T. Y. et al. (1971) *J. Biol. Chem.* 246:2849–58; Liu, T. Y. et al. (1971) *J. Biol. Chem.* 246:4703–12]. Meningococci of serogroups B, C, Y, and W-135 express capsules composed entirely of polysialic acid or sialic acid linked to glucose or galactose [Liu, T. Y. et al. (1971) *J. Biol. Chem.* 246:4703–12; Bhattacharjee, A. K. et al. (1976) *Can. J. Biochem.* 54:1–8], while the capsule of group A *N. meningitidis* is composed of N-acetyl mannosamine-1-phosphate [Liu, T. Y. et al. (1971) *J. Biol. Chem.* 246:2849–58]. The currently available capsular polysaccharide vaccines for serogroups A, C, Y, or W-135 *N. meningitidis* are effective for control of meningococcal outbreaks in older children and adults. However, because of poor immunogenicity in young children and short-lived immunity [Zollinger, W. D. and Moran, E. (1991) *Trans. R. Soc. Trop. Med. Hyg.* 85:37–43], these vaccines are not routinely used for long-term prevention of meningococcal disease. In the case of group B *N. meningitidis*, whose ($\alpha 2 \rightarrow 8$)-linked polysialic capsule is an immunotolerized self antigen, a reliable polysaccharide vaccine is not yet available. However, rapid progress is being made in development of polysaccharide-protein conjugate vaccines and it is hoped that following the example of newly licensed *Haemophilus influenzae* type b vaccines, widespread introduction of the polysaccharide conjugates will lead to elimination of disease.

In some epidemic settings, simultaneous or closely-linked meningococcal outbreaks have occurred in the same population due to different serogroups [Sacchi, C. T. et al. (1994) *J. Clin. Microbiol.* 32:1783–1787; CDC (1995) *MMWR* 44:121–134; Krizova, P. and Musilek, M. (1994) *Centr. Eur. J. Publ. Hlth* 3:189–194]. Further, Caugant et al. (Caugant, D. A. et al. (1986) *Proc. Natl. Acad. Sci. USA* 83:4927–4931; Caugant, D. A. et al. (1987) *J. Bacteriol.* 169:2781–2792] and others have noted that meningococcal isolates of different serogroups may be members of the same enzyme type (ET)-5, ET-37 or ET-4 clonal complexes.

Since 1993, the number of cases of serogroup B meningococcal disease in Oregon and adjacent counties in Washington State has doubled, and the overall incidence has been five-fold higher than rates observed in other parts of the United States [CDC (1995) *MMWR* 44:121–134]. This increase was due to the first appearance in the U.S. of serogroup B meningococcal strains closely related to the ET-5 complex. ET-5 complex strains have been responsible for major epidemics in Norway, Iceland, Cuba and South America over the last twenty years (Caugant, D. A. et al. (1986) *Proc. Natl. Acad. Sci. USA* 83:4927–4931; Sierra, G. V. et al. (1991) *NIPH Annals* 14:195–207; Sacchi, C. T. et al. (1992) *J. Clin. Microbiol.* 30:1734–1738]. Since 1994, cases of serogroup C meningococcal disease due to ET-5 complex strains were also noted in Oregon and Washington State. There exists a recurring need to understand the genetic basis for meningococcal capsule expression and to analyze the serogroup B and C ET-5 meningococcal strains responsible for the outbreak in the Pacific Northwest.

SUMMARY OF THE INVENTION

It is an object of the present invention to provide strains of *N. meningitidis* of a particular serogroup transformed in vitro to express a capsule polysaccharide marker of a different meningococcal strain serogroup. In a particular embodiment are provided prototype serogroup C, Y and W-135 meningococcal strains transformed in vitro with DNA comprising the synD of the serogroup B strain NMB. According to the present invention, conversion from one sialic acid expressing capsule serogroup to another can be accomplished by homologous recombination of the sequences encoding the serogroup-specific capsule polymerase. Such recombinant *N. meningitidis* strains are provided according to the invention as genetically engineered in vitro recombinations.

Also provided by the present invention are *Neisseria meningitidis* mutant serogroup strains which express different non-isogeneic capsular polysaccharides due to homologous recombination of the sequences encoding the serogroup-specific capsule polymerase. Specifically exemplified herein is a mutant N. meningitidis strain 1070 (serogroup B, ET-301) in which genetic markers are isogeneic to serogroup B except for the capsule polysaccharide, which is a serogroup C marker. Such meningococcal isolates comprise a recombinant or switched capsule gene and, in a particular embodiment, a switching or recombination event occurred from a serogroup B to a serogroup C capsule biosynthetic gene. Such recombinant N. meningitidis strains are provided according to the invention as naturally-occurring in vivo recombinant isolates.

It is also an object of the invention to provide meningococcal serogroup-specific capsule genes encoding characteristic capsular polysaccharide virulence determinants. In specific embodiments of the invention are provided capsule biosynthetic gene preparations of prototype serogroups A, B, C, Y and W-135, each serogroup-specific gene encoding a biosynthetic enzyme for a specific and distinguishing capsular polysaccharide.

It is an additional object of the invention to provide cloned DNA molecules which can be used to introduce an additional non-isogeneic capsular polysaccharide virulence determinant into strains of N. meningitidis. In a particular embodiment, the cloned DNA fragment containing the stable Tn916 insertion in the synD of the serogroup B N. meningitidis strain NMB was used to introduce the gene for the serogroup B ($\alpha2 \rightarrow 8$)-linked capsule polysialyltransferase into other meningococcal strains to produce novel immunotypes. More generally, a cloned DNA fragment containing a stable insertion of a polysialyltransferase gene of a specific serogroup strain can be used to introduce the corresponding capsular polysaccharide determinant into serologically different strains to produce novel immunotypes. This invention also contemplates that multiple non-isogeneic capsular polysaccharide virulence determinants can be introduced into serologically different meningococcal strains.

The present invention provides the nucleotide sequence of the intergenic region separating ctrA from the biosynthesis operon (synA-D,E,F,G) of a serogroup A N. meningitidis. Whereas in serogroups B, C, Y and W-135 N. meningitidis, the intergenic region separating ctrA from the biosynthesis operon (synA-D,E,F,G) is 134 bp and contains the ctrA-D promoter as well as the divergent biosynthesis operon promoter and other transcriptional regulatory elements, in serogroup A N. meningitidis the intergenic region is 218 bp in length and does not share any homology with the 134 bp region found in the sialic acid capsular serogroup stains.

This invention also provides evidence that the DNA located between ctrA and galE in serogroup A N. meningitidis is a cassette containing four genes ORF1–ORF4 responsible for the production of serogroup A capsule from UDP-N-acetylglucosamine. Also the organization of, and the amino acid sequences encoded by, the ORF1–ORF4 are provided by the present invention.

Further, according to this invention, the ORF1–ORF4 genes are divergently co-transcribed from overlapping promoters located in a short intergenic region separating the capsule biosynthetic and transport operons. Mutagenesis of these genes results in a capsular phenotype, demonstrating the critical involvement of these genes in serogroup A capsule production.

The invention also provides a model in which meningococcal capsular serogroups are determined by specific biosynthesis genetic cassettes that insert between the ctrA operon and galE. In specific embodiments, it is demonstrated for serogroup A meningococci that the cassettes determining specificity of serogroups can recombine to switch the type of capsule and serogroup expressed. Such information is critical to the design of improved group A and other meningococcal vaccines and to the understanding of the molecular basis of serogroup A pathogenesis.

Also provided are compositions and immunogenic preparations including but not limited to vaccines, as specifically exemplified, comprising at least one capsular polysaccharide derived from one serogroup strain of N. meningitidis and at least one capsular polysaccharide from a different meningococcal serogroup strain, and a suitable carrier therefor are provided. Alternatively, the immunogenic composition can comprise cells of at least two different serotype strains of the specifically exemplified N. meningitidis strains and a suitable carrier.

It is an added object of the present invention to provide protective immunity from virulent meningococcal strains that may not be recognized by traditional serogroup-based surveillance and that can escape vaccine-induced or natural protective immunity by capsule switching. In particular embodiments, the invention provides multivalent vaccines anticipating capsule switching events. According to the invention, broad immunization with capsular polysaccharide vaccines effective against all major capsular serogroups can be used to control epidemics and endemic disease.

It is yet another object of the invention to provide a method for diagnostic detection and serogroup typing of N. meningitidis strains. This method is a nucleic acid amplification (e.g., PCR) method or nucleic acid hybridization method based on (a) the specific nucleotide and encoded amino acid sequences of serogroup-specific capsular polysaccharide determinants and (b) oligonucleotide primers designed to anneal to specific capsule polymerase sequences. This method of the invention was particularly exemplified in the typing of N. meningitidis serogroups A,B,C, Y and W-135. This nucleic acid amplification method of the invention, based on the use of discriminatory primers derived from serogroup-specific nucleotide sequences (Sequo-grouping) offers advantages over current methods of diagnostic detection of serogroup typing in (a) being independent of the need to grow pathogenic organisms for immunological analyses, (b) being capable of being performed directly on clinical specimens, e.g., blood cerebrospinal fluid, with the need to isolate pathogenic organisms, (c) being capable of detecting nucleotide sequences in not only living but also nonliving or nonviable organisms, (d) reducing the exposure of personnel to large volumes of pathogenic bacteria, (e) reducing the cost per serogroup analysis, and (f) improving significantly the accuracy of the serotyping method. This method is particularly preferred as an easy, convenient and rapid screening method for the presence of virulent strains of encapsulated pathogens.

BRIEF DESCRIPTION OF THE FIGURES

FIG. 1A illustrates the genetic basis for serogroup B meningococcal capsular polysaccharide. Meningococcal capsules are produced by genes encoded by the 24 kb cps gene complex comprising five regions: E, C, A, D, and B. In serogroup B, four capsular biosynthetic genes (synX-D) are found in region A and are transcribed as an operon. Region C, adjacent to region A, contains 4 polycistronic genes, ctrA-D, encoding proteins which transport the phospholipid-substituted polysialic acid across the inner and outer membranes. The ctr genes are transcribed in the opposite orientation from the syn biosynthetic genes of region A, but utilize the same 134 bp promoter region [Swartley et al. (1996) *J. Bacteriol.* 178:4052–4059].

FIG. 1B illustrates the biosynthetic pathway for the production of serogroup B capsule; SynX is either the N-acetyl-D-glucosamine-6-phosphate 2-epimerase which produces N-acetyl-D-mannosamine-6-phosphate or a specific phosphatase which converts N-acetyl-D-mannosamine-6-phosphate into N-acetyl-D-mannosamine [Swartley, J. S. and Stephens, D. S. (1994) *J. Bacteriol.* 176:1530–1534]; SynB is the CMP-N-acetylneuraminic acid (NANA) synthetase [Edwards, U. and Frosch, M. (1992) *FEMS Microbiol. Lett.* 96:161–166]; SynC is the NANA synthetase [Ganguli, S. et al. (1994) *J. Bacteriol.* 176:4583–89]; and SynD is the polysialyltransferase responsible for (α2→8)-linked polysialic acid chain polymerization and elongation [Frosch et al. (1991) *Mol. Microbiol.* 5:1251–1260].

FIG. 1C illustrates Southern DNA hybridization showing ctrA homology in serogroups A (strains F8229, F8239), B (strains NMB, 1070 [B-301*]), C (strains FAM 18, 1205 [C-301*], 1843 [C-301]), Y (strain GA0929), and W-135 (strain 6083) of *N. meningitidis*. Chromosomal DNA from each of the strains was prepared, digested with Cla1, electrophoresed through a 1.2% agarose gel and transferred to a nylon membrane. The membrane was then probed with a 150 bp digoxigenin-labeled PCR product derived from the 5'-end of the serogroup B ctrA gene. *N. lactamica* and *N. gonorrhoeae* (GC) showed no hybridization. Molecular weight size standards (Boehringer Mannheim Biochemical) flank the chromosomal digests.

FIG. 1D illustrates PCR amplification of ctrA and synX-synD from serogroups A (strain F8239), B (strain NMB), C (strain FAM18), W-135 (strain 6083), and Y (strain GA0929) *N. meningitidis* using oligonucleotide primers derived from the individual gene sequences of serogroup B prototype strain NMB. Kb DNA ladders (BRL) flank the gel.

FIG. 2 presents multiple nucleotide sequence alignment of the 3' end of synC and downstream sequence in serogroups B (strain NMB) [SEQ ID NO:1], C (strain FAM18) [SEQ ID NO:2], W-135 (strain GA1002) [SEQ ID NO:3], and Y (strain GA0929) [SEQ ID NO:4] *N. meningitidis*. (Pretty multiple sequence comparison program of the Genetics Computer Group [GCGI sequence analysis package version 7.3.1 UNIX (Devereux et al. (1984) *Nucl. Acids Res.* 12:387–395]). In the consensus sequence [SEQ ID NO:5], consensus nucleotide matches (3 or more identical) at each position are indicated in upper case type, while differences from consensus are indicated by lower case type. Dots (... ) indicate gaps introduced by the analysis program to facilitate alignment. The synC termination codon (TAA) and the synDlElF start codons (ATG) are shown in bold type. The location of an IS1301 element located downstream of the synC gene in the otherwise identical sequence of a second serogroup W- 135 strain, 6083, is shown in the GA 1002 sequence by an A^. The complete sequence of synE derived from serogroup C strain FAM18 is available through the GenBank/EMBL nucleic acid database under accession number U75650.

FIGS. 3A and 3B–1 to 3B–3 present genetic analyses of serogroup B301 (strains 1070 and 1069) and C301 (strains 1205, 1198 and 1204) *N. meningitidis* recovered from the Oregon/Washington State outbreak.

FIG. 3A illustrates the nucleotide sequence alignment of the 3'-end of synC and downstream sequence in serogroup B strains NMB (SEQ ID NO:1, positions 1–277) and 1070 (B-301#1) [SEQ ID NO:6], and serogroup C strains FAM18 (SEQ ID NO:2, positions 1–275) and 1205 (C-301#1) [SEQ ID NO:7] (Pretty multiple sequence comparison program of the Genetics Computer Group [GCG] sequence analysis package version 7.3.1 UNIX [Devereux et al. (1984) supra]). The synC termination codon (TAA) and the synDIE start codons (ATG) are indicated in bold type. The consensus sequence corresponds to SEQ ID NO:29.

FIGS. 3B–1 to 3B–3 illustrate nucleotide polymorphisms of the B301, C301 and other meningococcal strains. FIG. 3B1 illustrates polymorphisms within a 909 bp PCR product containing the 5'-ends of both ctrA and synX and the 134 bp intergenic region separating these two genes (bps 1–319 are the 5' end of ctrA, bps 320–453 are the 134 bp intergenic region, and bps 454–909 are the 5' end of synX) (Swartley et al. (1996) *J. Bacteriol.* 178:4052–4059]. FIG. 3B2 illustrates polymorphisms within a 238 bp PCR product amplified from the 330 bp FKBP gene (McAllister et al. (1993) *Mol. Microbiol.* 10:13–23), and 3) an 803 bp PCR product amplified from the 1128 bp recA gene (Zhou et al. (1992) Mol. Microbiol. 6:2135–2146). Regions were sequenced from strains 1070 (B301 # 1) (B), 1069 (B301 #2) (B), FAM18 (C), 1205 (C301 # 1) (C), 1198 (C301#2) (C), 1204 (C301#3) (C) GA1002 (W-135), F8239 (A), GA0929 (Y), and GA1002 (W-135) and compared to the sequence of other neisserial strains (McAllister et al. (1993) supra; Zhou et al. (1992) supra). The sequence of strain 1070 (B301#1) was used as the master sequence. Differences from the master sequence are indicated at the nucleotide positions within FKBP, recA, or the ctrA-synX PCR product, identity at a given position is indicated by a dash (-) and deleted nucleotides are shown by dots (...).

FIGS. 4A–4B present a 5064 base pair (bp) [SEQ ID NO: 8] of serogroup A *N. meningitidis* strain F8229. This sequence extending between ctrA and galE (as illustrated schematically in FIG. 5) comprises four ORFs distinct to genomes of the serogroup A. ORF1 is separated from ctrA by a 218 bp intergenic region. ORF1, extending from nucleotide 479 to 1597, is 1119 nucleotides long and encodes a protein of 373 amino acids [SEQ ID NO: 9]. ORF2, separated from ORF1 by one nucleotide, is 1638 bp in length (from nucleotide 1599 to nucleotide 3236) and encodes a 546 amino acid protein [SEQ ID NO: 10]. ORF2 is separated by 72 bp from ORF3 having 744 bp (nucleotides 3309–4052) and encoding a protein [SEQ ID NO: 12]. of 248 amino acids. ORF3 is separated by a single nucleotide from ORF4 (nucleotides 4054–4917) having 864 bp encoding a 288 amino acid protein.

FIGS. 5A–5B present the amino acid sequence [SEQ ID NO: 9]of a protein encoded by ORF1 [SEQ ID NO: 8]of serogroup A *N. meningitidis* F8229.

FIGS. 6A–6B present the amino acid sequence of [SEQ ID NO: 10]a protein encoded by ORF2 [SEQ ID NO: 8]of serogroup A *N. meningitidis* F8229.

FIG. 7 presents the amino acid sequence [SEQ ID NO:11] of a protein encoded by ORF3 [SEQ ID NO:8] of serogroup A *N. meningitidis* F8229.

FIG. 8 presents the amino acid sequence [SEQ ID NO:12] of a protein encoded by ORF4 [SEQ ID NO:8] of serogroup A *N. meningitidis* F8229.

Figure 1A:
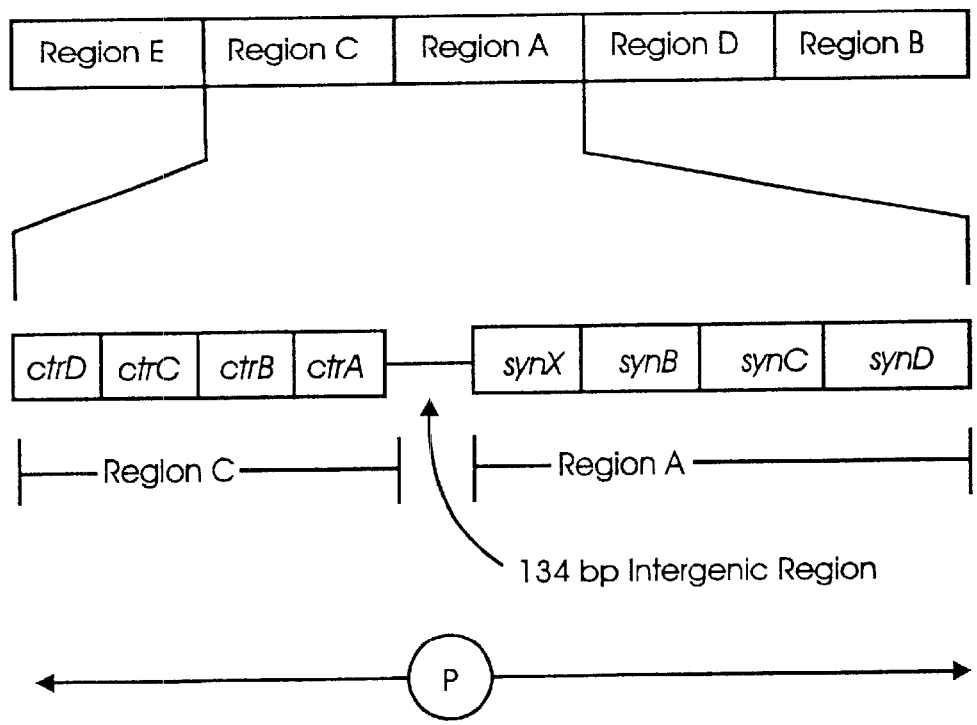
FIGS. 1A–1D present schematically molecular analysis of capsule biosynthesis and membrane transport genes in prototype isolates of serogroup A, B, C, Y and W-135 N. meningitidis.
Figure 1B:
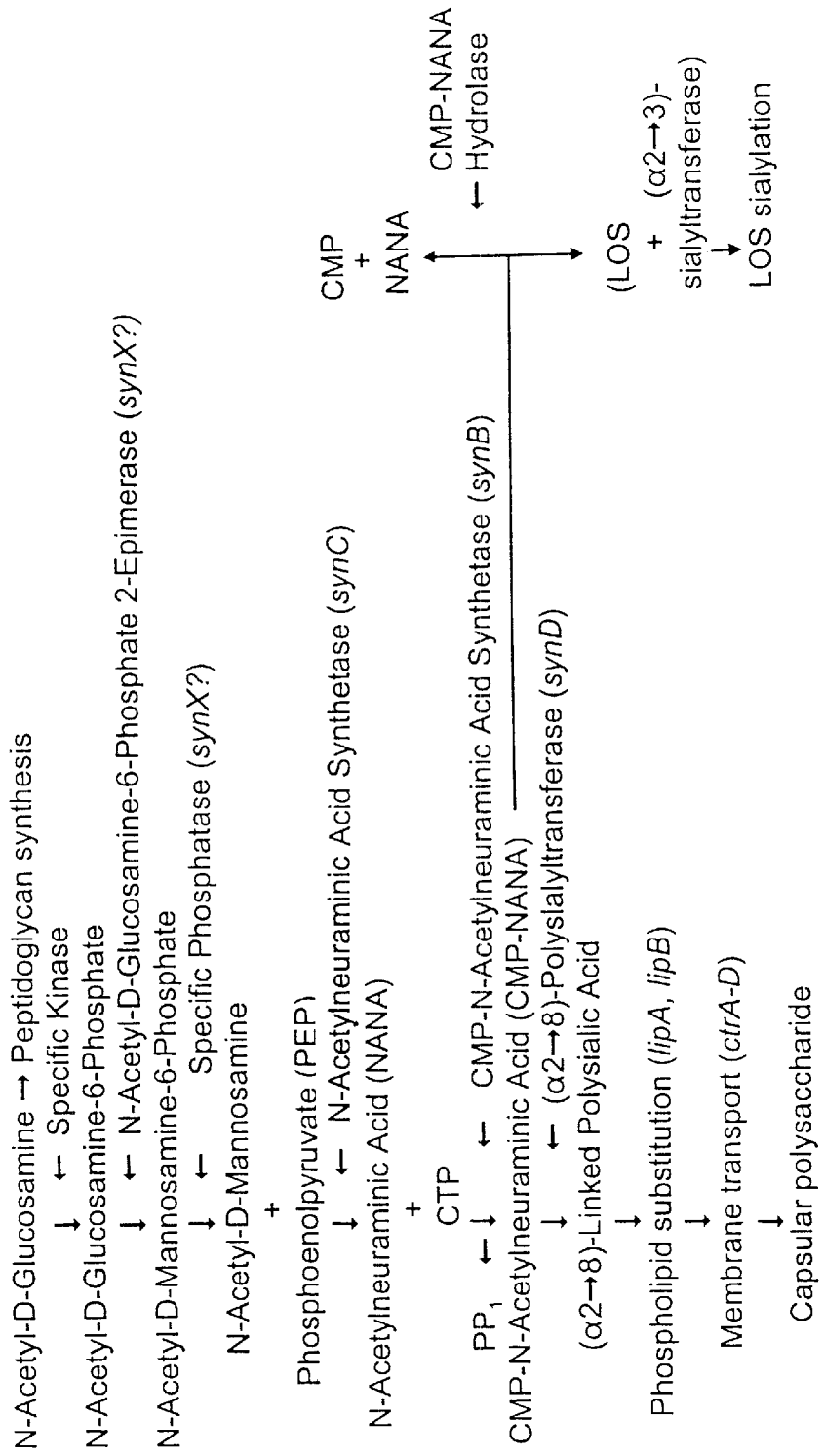

The role of these genes in the serogroup B capsule synthesis pathway is shown in FIG. 1B. SynX is either the N-acetyl-D-glucosamine-6-phosphate 2-epimerase that produces N-acetyl-D-mannosamine-6-phosphate or a specific phosphatase that converts N-acetyl-D-mannosamine-6-phosphate into N-acetyl-D-mannosamine. SynB is the CMP-N-acetylneuraminic acid (NANA) synthetase. SynC is the NANA synthetase and SynD is the polysialyltransferase responsible for ($\alpha 2 \rightarrow 8$)-linked polysialic acid chain polymerization and elongation.

Figure 1C:
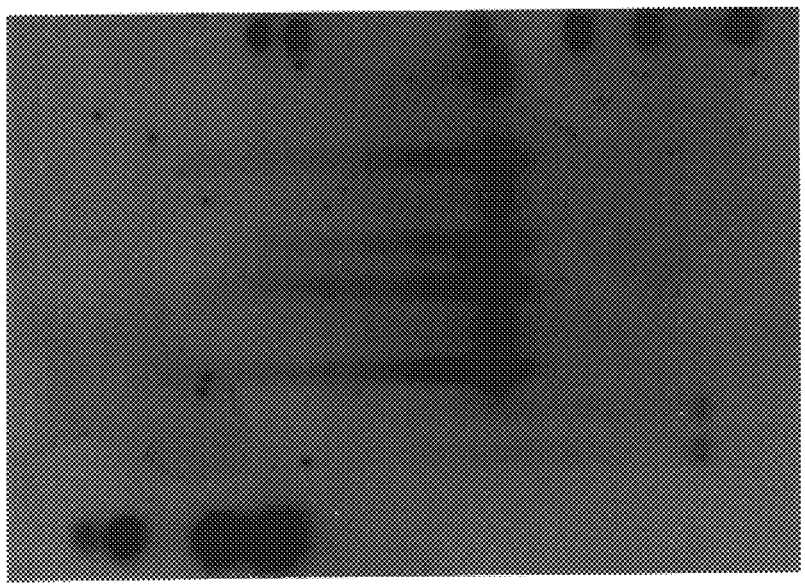
Figure 1D:
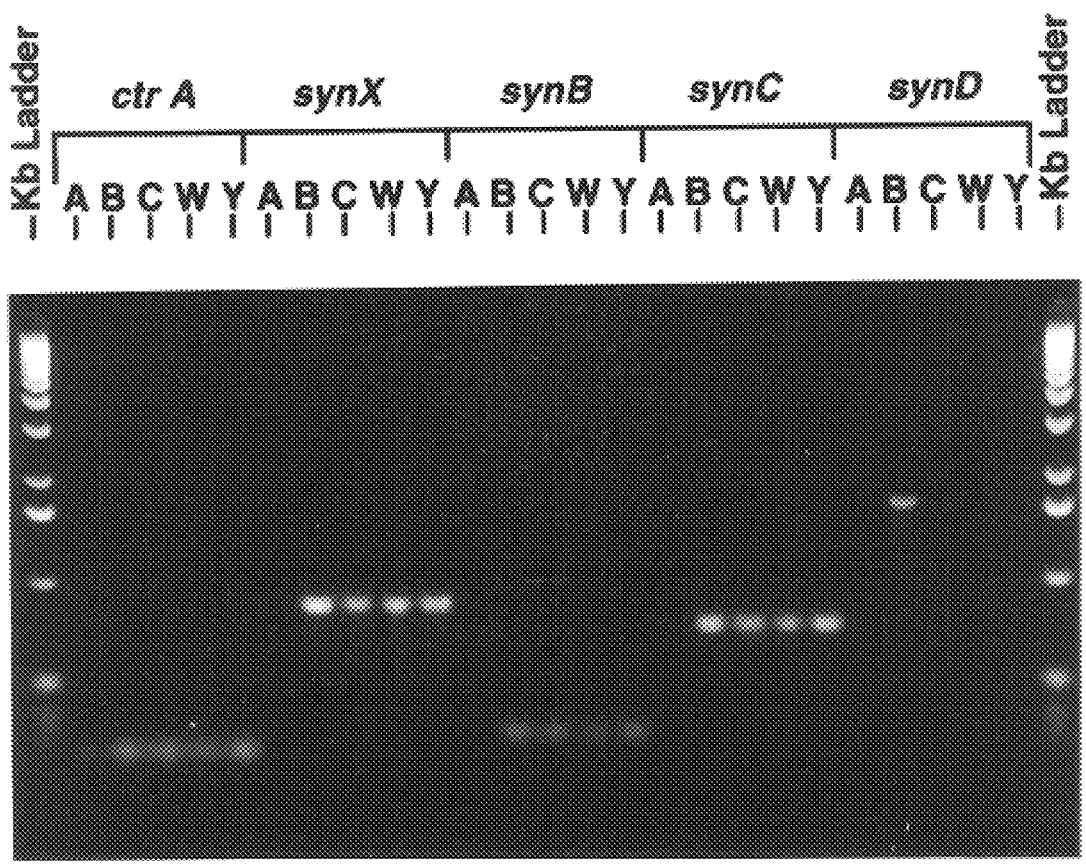
Figure 9:
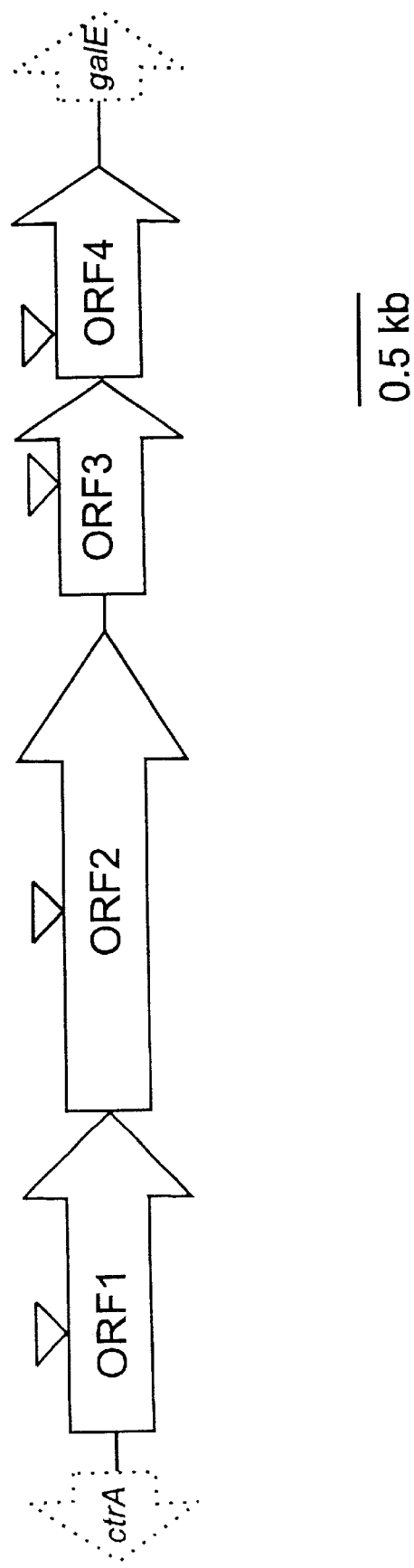
FIG. 9 presents a schematic illustrating the arrangement of four ORFs located between ctrA and galE. The four ORFs are transcribed in the opposite direction with respect to ctrA.
Figure 10:
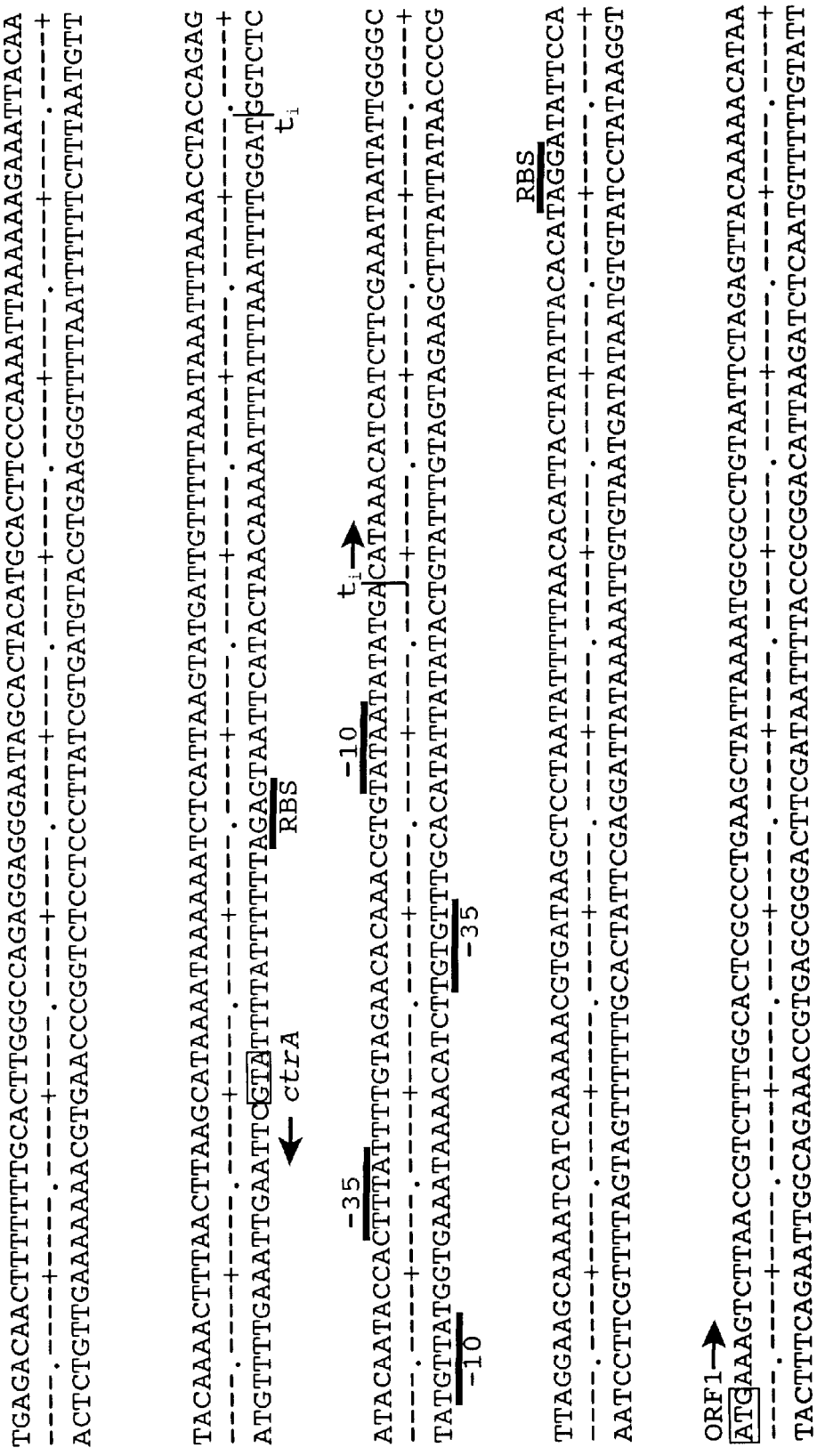
FIG. 10 presents the nucleotide sequence [SEQ ID NO:35] of the 218 bp intergenic region separating the start codons for the serogroup A ctrA and ORF1 loci. The start points and direction of transcription of the ORF1 and ctrA mRNA are indicated by $t_i$ and a right- or left-hand arrow, respectively. Predicted −10 and −35 promoter binding sequences are indicated, as well as the putative Shine-Dalgarno ribosome binding sites (RBS). The predicted initiation codons for ctrA and ORF1 are shown in boxes.

The genetic structure of the capsule transport and biosynthetic regions was assessed with Southern analysis, PCR and DNA sequencing in strains from each of the other major meningococcal serogroups as shown in FIGS. 1C and 1D. The strains of the sialic acid capsule-expressing serogroups (B, C, Y, W-135) were found to have a similar genetic organization consisting of the ctrA capsule transport gene linked by a short intergenic region to the oppositely transcribed biosynthetic genes synX-synC. Identical Southern hybridization patterns were obtained for ctrA (FIG. 1C), synX, synB and synC; identical PCR amplification products (FIG. 1D) were obtained for ctrA, synX, synB and synC; and similar nucleotide sequences were obtained for ctrA-synX intergenic region. These facts of identity established that ctrA and synX-C in serogroups C, Y, and W-135 *N. meningitidis* were homologues of the corresponding genes in serogroup B meningococci. In contrast, synd [the serogroup B ($\alpha 2 \rightarrow 8$)-linked capsule polysialyltransferase [Frosch et al. (1991) *Mol. Microbiol.* 5:1251–1260] was not detected in the serogroup C, Y and W-135 strains by Southern hybridization or PCR amplification using probes specific for synD of serogroup B (FIG. 1D).

Further, the nucleotide sequence of the 3' end of synC and the sequence downstream of synC were determined in serogroups C, Y, and W-135. The sequences of the 3' end of sync from serogroups B, C, Y, and W-135 were identical up to the last codon where the sequences then diverged (FIG. 2). The 5' ends of the downstream ORF's which encode the putative sialic acid capsule, polymerases (designated in serogroup B as synD, in serogroup C as synE, and in serogroups Y and W-135 as synF), were distinct (FIG. 2). In the serogroup Y and W-135 strains, the codon for the last amino acid in synC had been replaced by a different codon (creating a change from glutamine to serine). The nucleotide sequences downstream of synC were almost identical in serogroups Y and W-135 both in the intergenic region and in the first 800 bases of the 5'-end of the predicted capsule polymerase, but were distinct from serogroups B and C.

Thus, meningococci expressing serogroup B, C, Y, or W-135 sialic acid capsules have similar synX-C biosynthetic genes which are linked to ctrA of the capsule membrane transport operon. However, the genes encoding the sialic acid capsule polymerases in serogroups B, C, and Y/W-135 are different. Meningococci of serogroups Y and W-135 are almost identical in the 5'-end of this gene. These are known to be closely related serogroups and simultaneous elaboration of both serogroup W-135 and Y capsular polysaccharides by a single strain of *N. meningitidis* has been reported [Brandt et al. (1980) *J. Gen. Microbiol.* 118:39–43].

In contrast to the sialic acid producing serogroups, serogroup A meningococci contain a ctrA homologue but do not have a ctrA-synX intergenic region or the sialic acid biosynthetic homologues synX-synD homologues. The serogroup A ctrA differs in nucleotide sequence and Southern Cla1 fragment size from the sequence and location of ctrA in the sialic acid capsule-expressing serogroups (FIG. 1C). Instead of exhibiting a 134 bp intergenic region separating ctrA from synX as found in all of the sialic acid producing serogroups (B, C, Y and W-135), the serogroup A ctrA gene is preceded by a 218 bp intergenic region. The serogroup A intergenic region separates ctrA from four novel co-transcribed open reading frames, which have been designated orf1, orf2, orf3 and orf4. Since serogroup A does not produce a sialic acid containing capsule, the biosynthetic genes are different from those of serogroups B, C, Y and W-135. The serogroup A biosynthetic genes are only found in serogroup A and not in the other meningococcal serogroups. Southern and PCR analysis revealed that for a specific serogroup, the genes (e.g., synD, synE, synF) involved in alternative capsule polymerization were not present elsewhere in the chromosome (e.g., serogroup B strains contains synD but not synE or synF homologues.

The meningococcal capsule biosynthesis operon can be transformed in vitro. Meningococci are naturally competent for transformation. Conversion from one sialic acid expressing capsule serogroup to another was accomplished by homologous recombination of the sequences encoding the serogroup-specific capsule polymerase. Chromosomal DNA containing a Class I Tn916 insertion interrupting synD of the serogroup B strain NMB [Swartley et al. (1996) *J. Bacteriol.* 178:4052–4059] was prepared and used to transform [Swartley et al. (1993) *Mol. Microbiol.* 10:361–3693] the prototype serogroup C, Y, and W-135 meningococcal strains. Tetracycline-resistant transformants were obtained at a frequency of between $1 \times 10^{-5}$ and $1 \times 10^{-7}$/recipient. Acquisition of the Tn916 mutation and the adjacent synD sequence was confirmed by PCR and nucleotide sequence analysis of selected tetracycline-resistant transformants of these strains. Induced excision of the Tn916 transposon insertion restores synD activity at a frequency of approximately $1 \times 10^{-4}$. Restoration of synD resulted in the expression of ($\alpha 2 \rightarrow 8$)-linked polysialic acid capsule in an otherwise isogeneic serogroup C prototype strain.

The ability to transform a meningococcal capsule biosynthesis operon in vitro suggested an in vivo occurrence of such an event. The capsule biosynthesis and other genes in serogroup B and serogroup C ET-5 complex strains from the Pacific Northwest outbreak were analyzed for the possibility that a transformation event involving the capsule biosynthesis genes might have produced the closely related serogroup B and C meningococcal strains recovered in the Oregon and Washington State outbreak. The analysis included the capsule biosynthetic and transport operons as well as unlinked genes in two serogroup B and three serogroup C ET-5 complex strains (Table 1) recovered from this outbreak. These strains by ET-type (301), serotype (15), subtype (1.7,16), immunotype (L3,7,9), and PFGE type were identical; they differed only in the type of capsule produced.

TABLE 1

N. meningitidis isolates of the ET-5 complex recovered from patients with invasive meningococcal disease in Oregon in 1994

| ID no. | Date of onset of illness | Sero-group | Serotype | Subtype | Immuno-type | ET type | PFGE type |
|---|---|---|---|---|---|---|---|
| B301#1 1070 | 06/21/94 | B | 15 | 1.7, 16 | L3, 7, 9 | 301 | A |
| B301#2 1069 | 06/13/94 | B | 15 | 1.7, 16 | L3, 7, 9 | 301 | A |
| C301#1 1205 | 11/19/94 | C | 15 | 1.7, 16 | L3, 7, 9 | 301 | A |
| C301#2 1198 | 08/08/94 | C | 15 | 1.7, 16 | L3, 7, 9 | 301 | A |
| C301#3 1204 | 10/29/94 | C | 15 | 1.7, 16 | L3, 7, 9 | 301 | A |

The capsule biosynthesis operon was analyzed in the different strains. By PCR and Southern hybridization profile, the strains showed similar ctrA and synX-C homologues, but the serogroup B ET-301 strains contained a synD homologue, whereas the serogroup C ET-301 strains contained a synE homologue. This observation was confirmed by determination of the nucleotide sequences of the intergenic region following synC as well as the sequences of the 5'-end of the downstream gene encoding the predicted polysialyltransferase. As shown in FIG. 3A, these regions were distinct in strain 1070 (serogroup B, ET-301) and 1205 (serogroup C, ET-301) isolates, exhibiting only 63% nucleotide identity. However, the nucleotide sequence of synD in the B301 strain was 99% identical to synD of the prototype serogroup B strain NMB; and in the C301 strain, synE was 99% identical to synE of the prototype serogroup C strain FAM18. Nucleotide sequences of synX and synC from strains 1070 and 1205 demonstrated 1% (synX) and 5% (synC) diversity (FIGS. 3A and 3B1) suggesting that in addition to the polysialyltransferase, the entire synX-D biosynthetic operon had exchanged.

The extent of the recombinational event was determined by analyzing other operons. In contrast to the biosynthesis operon, the 5' nucleotide sequence of ctrA and the ctrA-synX intergenic region were identical in B-301 strains 1070 and 1069 and C-301 strains 1205, 1198 and 1204, but differed from other B, C, Y, and W-135 strains (FIG. 3B1). For example, the two B-301 and three C-301 strains contained the same synX-ctrA intergenic nucleotide sequence including an 8 bp deletion. In addition, the nucleotide sequence of two genes (recA [Zhou et al. (1992) Mol. Microbiol. 6:2135–2146] and fkbp [McAllister et al. (1993) Mol. Microbiol. 10:13–23]) not linked to capsule expression were also identical in the B-301 and C-301 strains, but the sequence differed by up to 5% from other meningococcal strains (FIG. 3B2 and FIG. 3B3).

Thus, capsule switching of the epidemic serogroup B/C isolates was the result of substitution of the serogroup B synD polysialyltransferase with the serogroup C synE polysialyltransferase. Upstream of the polysialyltransferases, the recombinational event also appeared to have included the conserved CMP-NANA biosynthesis genes, synX-synC, but did not extend to ctrA or the intergenic region separating ctrA-synX, and did not involve unlinked genes. The downstream recombinational exchange did not appear to have occurred in galE. PCR studies using primers specific for the 3' end of synC and the 5' end of galE [Zhou et al. (1994) J. Biol. Chem. 269:11162–11169] indicated that synD/E were downstream from galE by approximately 2 kb in the prototype serogroup B strain, NMB, in the prototype serogroup C strain, FAM18, and in each of the B-301 and C301 strains. However, PCR amplification of chromosomal DNA using internal galE-specific primers derived from the NMB galE sequence [Zhou et al. (1994) supra] yielded a 900 bp product; but this product was not obtained with the serogroup C prototype strains FAM18, and two other non-ET-301 serogroup C strains (GA0078-ET-17, GA0290, ET-27).

This invention provides data indicating that capsule switching in N. meningitidis can occur by gene conversion of the capsule polymerase and that this event occurs in vivo. Presumably, co-colonization of serogroup B and C strains in the human nasopharynx and genetic exchange of capsule biosynthesis genes by transformation and allelic-exchange is the event responsible for capsule switching. The high frequency (5–10%) of meningococcal carriage in the human nasopharynx of adults [Greenfield et al. (1971) J. Infect. Dis. 123:67–73], which appears to increase in epidemic settings, may facilitate the chances of capsule switching. There are meningococcal strain collections which contain isolates with identical genetic markers (e.g., ET-type) but that express different capsular polysaccharides. In addition to the meningococcal epidemic in the Pacific Northwest, recent cases in the Czech Republic and Canada [Kriz, P. and Musilek, M. Abstracts of the Tenth International Pathogenic Neisseria Conference, Zollinger, W. D., Frasch, C. E. and Deal, C. D. (eds.), Poster 174, p. 482, Baltimore, Md.; Ashton, F. E. et al. (1996) Abstracts of the Tenth International Pathogenic Neisseria Conference, Zollinger, W. D., Frasch, C. E. and Deal, C. D. (eds.), Poster 148, p. 431, Baltimore, Md.] of meningococcal disease caused by B and C strains with identical serotypes and ET types suggest that capsule switching may be common. Indeed, the ability to switch capsules provides a selective advantage to meningococci, in as much as they are thereby able to evade killing, opsonization or neutralization by pre-existing anticapsular antibody. Moreover, capsule switching may not be an isolated event in meningococci, but appears to occur in encapsulated Streptococcus pneumoniae and Haemophilus influenzae [Coffey, T. J. et al. (1991) Mol. Microbiol. 5:2255–2260; Kroll, J. S. and Moxon, E. R. (1990) J. Bacteriol. 172:1374–1379].

The nucleotide sequence [SEQ ID NO:8, presented in FIGS. 4A–4B, spanning the region between ctrA and galE in the encapsulated serogroup A N. meningitidis strain F8229, was determined using a combination of standard and single-specific-primer (SSP)-PCR. Primer LJ4, which anneals to sequence complementary to the 5' end of ctrA (Table 2) was used to begin "chromosome walking" 2.2 kilobases (kb) upstream of ctrA in strain F8229 by SSP-PCR. Next, primer SE33, designed to anneal to the 3' end of the 2.2 kb region, and primer GalE1, designed to anneal to sequence complementary to the 5' end of galE, were used to PCR amplify an additional 2.5 kb of intervening DNA. The double-stranded sequence of the 5064 bp stretch separating ctrA from galE in serogroup A *N. meningitidis* was determined from these products and confirmed by a combination of manual and automated DNA sequencing methods.

TABLE 2

| Primer Name | Nucleotide Sequence (5' → 3') | SEQ ID NO: |
|---|---|---|
| LJ4 | CCACCACCAAACAATACTGCCG | [SEQ ID NO:36] |
| SE33 | GTCAACTCAGAAGATAAGAATTGG | [SEQ ID NO:37] |
| SE35 | TCTCTTTTGTGATTCCGCTCC | [SEQ ID NO:38] |
| SE40 | GAATAGCACTACATGCACTTCCC | [SEQ ID NO:39] |
| SE41 | CAGGGCGAGTGCCAAAGACG | [SEQ ID NO:40] |
| SE46 | GAAGCTGTAGCTGCAGGAACTG | [SEQ ID NO:41] |
| SE56 | AATCATTTCAATATCTTCACAGCC | [SEQ ID NO:42] |
| SE57 | TTACCTGAATTTGAGTTGAATGGC | [SEQ ID NO:43] |
| SE58 | GTACCAATCAAAGGCGATATTGG | [SEQ ID NO:44] |
| SE61 | CAAAGGAAGTTACTGTTGTCTGC | [SEQ ID NO:45] |
| SE63 | TTCATATAACTTGCGGAAAAGATG | [SEQ ID NO:46] |
| JS102 | GAGCCTATTCGAAATCAAAGCTG | [SEQ ID NO:47] |
| JS103 | AGATACCATTAGTGCATCTATGAC | [SEQ ID NO:48] |
| JS104 | CATGAAACTCAGCACAGATAGAAC | [SEQ ID NO:49] |
| JS105 | GTTATTTAAATCTAGCCATGTGG | [SEQ ID NO:50] |
| galE1 | CGTGGCAGGATATTGATGCTGG | [SEQ ID NO:51] |

Computer analysis of the approximately 5 kb sequence indicated the presence of four ORFs transcribed in the opposite orientation with respect to ctrA. The first ORF (ORF1) was separated from ctrA by a 218 base pair (bp) intergenic region. ORF1 (nucleotides 479–1597) was 1119 nucleotides long and was predicted to encode a 372 amino acid protein [SEQ ID NO:9; FIGS. 5A–5B. ORF1 was separated by a single base from ORF2 (nucleotides 1599–3236), which was 1638 bp long, and was predicted to encode a 545 amino acid protein [SEQ ID NO:10; FIGS. 6A–6B. ORF2 was in turn separated by 72 bp from a 744 bp ORF, designated ORF3 (nucleotides 3309–4052), predicted to encode a 247 amino acid protein [SEQ ID NO:11; FIG. 7]. Finally, ORF3 was separated by a single nucleotide from an 864 bp ORF, designated ORF4 (nucleotides 4054–4917), which was predicted to encode a 287 amino acid protein [SEQ ID NO:12; FIG. 8]. The nucleotide sequences and predicted amino acid translations of ORF1–4 have been submitted to GenBank and are available under accession #AF019760. The organization of ORFs located between ctrA and galE is presented schematically in FIG. 9.

In addition to the sequence derived from encapsulated wild-type strain F8229, the first 2330 bp of the ctrA-galE intervening region in the unencapsulated serogroup A variant strain F8239 was also sequenced. Comparison of the nucleotide sequences derived from F8239 and F8229 indicated that they were nearly identical (11 nucleotide differences [7 deletions/additions, 2 transversions, 2 transitions] over the entire 2.2 kb stretch). However, in strain F8239, ORF1 was only 744 nucleotides long (247 amino acid predicted protein). Computerized alignment of the amino acid translation of the F8239 and F8229 ORF sequences indicated that in F8239, ORF2 was prematurely truncated by a frame-shift mutation.

Nucleotide and predicted amino acid sequences of the putative ORFs were compared to the GenBank/EMBL and FA1090 gonococcal genome project database. ORF1 showed best homology (57.6% amino acid identity) with a cytoplasmic *E. coli* protein designated NfrC. The 1131 bp nfrc gene encodes a 377 amino acid protein predicted to be a UDP-N-acetyl-D-glucosamine 2-epimerase (Kiino, D. R. et al., "A cytoplasmic protein, NfrC, is required for bacteriophage N4 adsorption [1993] *J. Bacteriol.* 175:7074–7080). ORF2 demonstrated predicted nucleotide and amino acid homology with two separate ORFs of unknown function, a 1125 bp open reading frame found downstream of galE/rfbBCD in serogroup B *N. meningitidis* (26.8% identity) and the 1632 bp cpsY of *Mycobacterium leprae* (37.7% identity). ORF3 and ORF4 did not exhibit significant nucleotide or predicted protein homology with any genes or proteins in the databases. Except for the partial ORF2 homology with an unknown ORF in serogroup B *N. meningitidis,* ORF1–4 were not present in the genomes of other meningococcal serogroups or *N. gonorrhoeae* by data base search, Southern hybridizations or PCR. It is proposed that ORF2 may be the polymerase linking individual UDP-ManNAc monomers together. The first biosynthetic step in the pathway is the production of UDP-ManNAc from UDP-NAc performed by the gene product of ORF1. ORF2 likely encodes the UDP-N-acetyl-mannosamine ($\alpha1\rightarrow6$) polymerase and ORF3 and ORF4 may be involved in further modification and assembly of the serogroup A capsule. It is proposed that ORF2 may be the polymerase linking individual UDP-ManNAc monomers together.

The biosynthesis of the serogroup A capsule of *N. meningitidis* requires genes that are not found in other meningococcal serogroups. However, the general overall genomic organization of the capsule transport and biosynthesis regions of serogroup A meningococci and of the sialic acid containing capsular serogroups (B, C, Y and W-135) is similar. In all serogroups, the genes of the ctr capsule transport operon are preceded by an intergenic region which separates etrA-D from an operon of divergently transcribed genes involved in capsule biosynthesis (SEQ ID NO:35; FIG. 10). These biosynthesis genes lie between ctrA and the gene encoding the UDP-glucose-4-epimerase (galE) necessary for LOS biosynthesis. Thus, differences in capsule composition between meningococcal serogroups are determined by proteins encoded in the distinct genetic cassettes located between ctrA and galE.

To determine whether ORF1–ORF4 were organized as an operon, RT-PCR determinations were performed on whole cell RNA obtained from strain F8229. It was shown that ORF1–ORF4 are co-transcribed on the same mRNA message, and therefore constitute an operon. The start site of transcription of the ORF1–ORF4 operon, as defined by primer extension (FIG. 11), was located within the 218 bp intergenic region separating ctrA and ORF1 (FIG. 12). The putative transcriptional start site was preceded by a putative σ-70-type promoter consensus sequence. The serogroup A ctrA transcriptional start site was also present in the 218 bp intergenic region as shown by primer extension (FIG. 11). It was also preceded by a near consensus σ-70-type promoter that overlapped the ORF1 promoter.

To confirm the role of ORF1–ORF4 in serogroup A capsule expression, insertion mutations were created in each of the ORFs in the wild-type encapsulated strain F8229. Strains F8229ORF1Ω, F8229ORF2Ω, F8229ORF3Ω, and F8229ORF4Ω were created by Ω-spectinomycin insertional mutagenesis of specific ORFs in wild-type encapsulated serogroup A strain F8229. Autoradiographs, shown in FIGS. 13A–13B, demonstrated that polar mutagenesis of all of the four ORFs in wild-type strain F8229 resulted in a reduction or loss of encapsulation. These data were confirmed using a quantitative capsule whole cell ELISA (Table 3).

Figure 11:
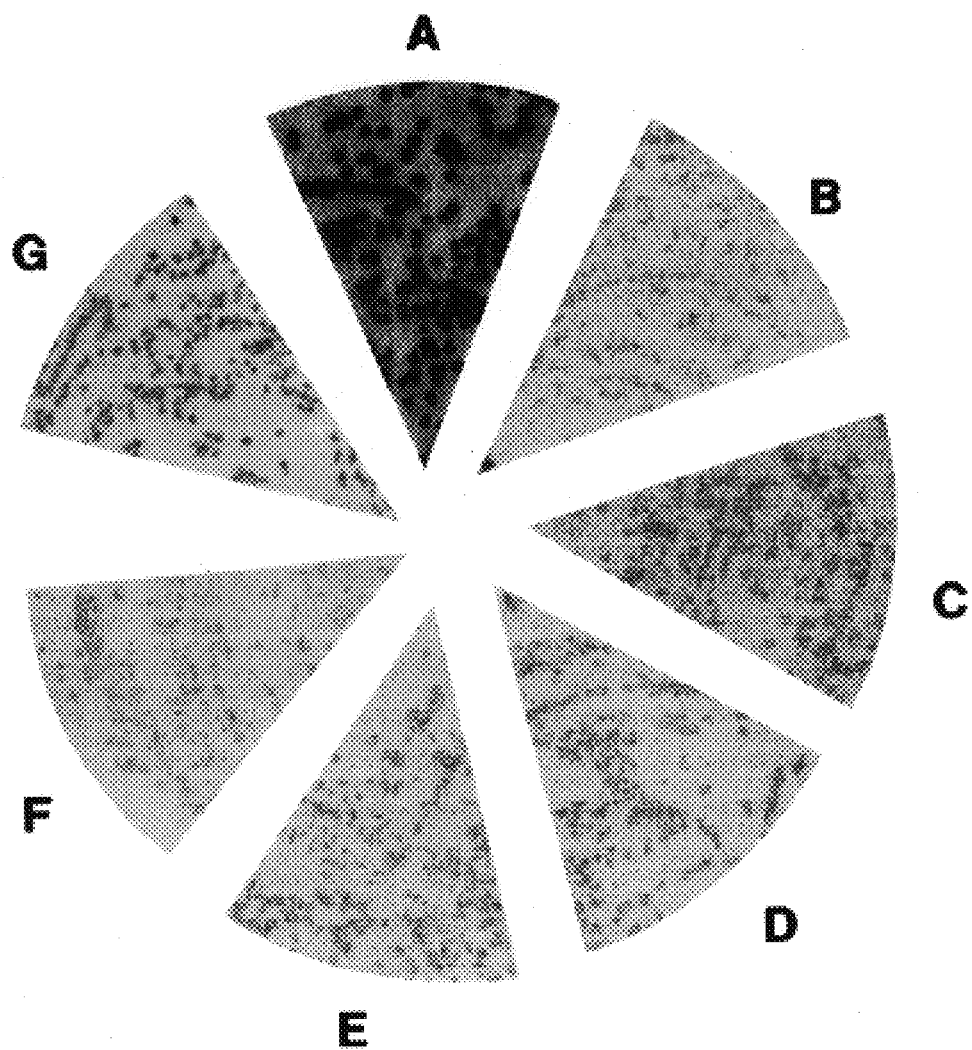
FIG. 11 presents colony immunoblots of wild-type and mutant strains of serogroup A N. meningitidis. Strains were grown overnight on GC base agar, transferred to nitrocellulose and probed with anti-serogroup A monoclonal antibody 14-1-A. Strain identities are as follows: (A) serogroup A wild-type encapsulated strain F8229, (B) serogroup A unencapsulated variant F8239, (C) F8229-ORF1Ω, (D) F8229-ORF2Ω, (E) F8229-ORF2apha-3 comprises regions A–E. Region C (membrane transport region) comprises four genes (ctrA to D) and region A (biosynthesis region) also comprises four genes (synX to D). The region C genes are separated from the region A genes by a 134 bp intergenic region which contains transcriptional start sites for both ctrA and synX preceded by promoter binding sequences. Regions C and A are divergently transcribed from the intergenic region.
Figure 12:
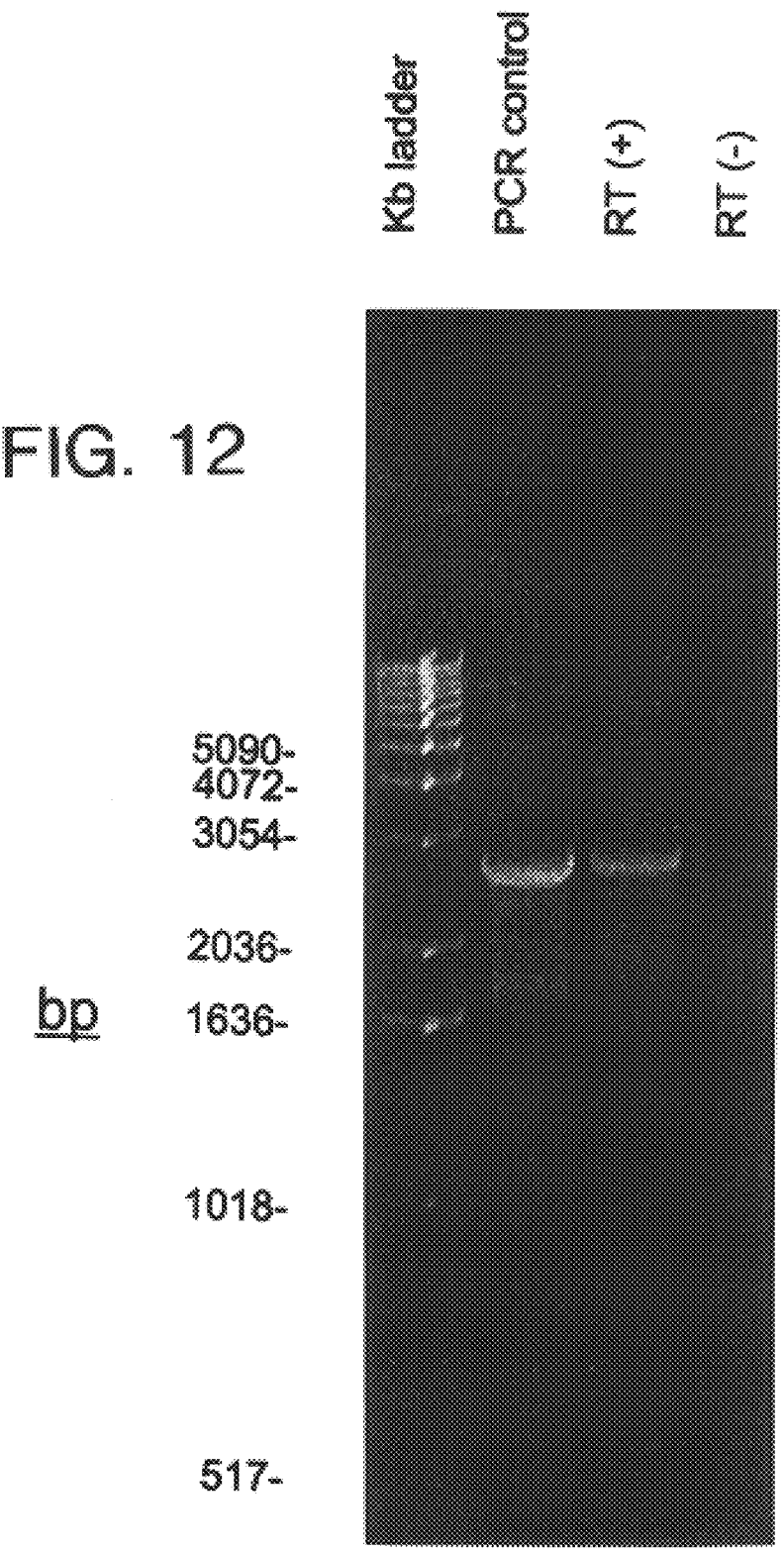

Attempts to create non-polar interruptions of ORF1 and ORF2 by integrating an aphaA-3 cassette into the same unique sites used for the Ω-cassette mutagenesis resulted only in the integration of this fragment into ORF2. Like the polar Ω-spectinomycin knock-out mutants, the non-polar interruption of ORF2 also resulted in a loss of group A capsule expression, as visualized by colony immunoblots and whole cell ELISA (strain F8229ORF2aph3, FIG. 11 and Table 3).

TABLE 3

| Strain | Mean $A_{405}$ | SD | % reduction vs wild-type |
| --- | --- | --- | --- |
| F8229 | 0.939 | 0.016 | N.A. |
| F8239 | 0.000 | 0.000 | 100% |
| F8229-ORF1Ω | 0.000 | 0.000 | 100% |
| F8229-ORF2Ω | 0.000 | 0.000 | 100% |
| F8229-ORF2aphA-3 | 0.000 | 0.000 | 100% |
| F8229-ORF3Ω | 0.000 | 0.000 | 100% |
| F8229-ORF4Ω | 0.101 | 0.007 | 89% |

The invention also provides a vaccine based on capsule polysaccharide structure and a method for vaccinating a population at risk during an epidemic outbreak. Further, the invention provides for epidemiologic investigations of disease due to encapsulated bacteria. For example, meningococci of different serogroups recovered during epidemic outbreaks or from cases of endemic disease can be identical in their expression of other virulence factors (e.g., outer membrane proteins) but express different capsular polysaccharides. Meningococcal capsule switching appears to occur among sialic acid-expressing strains by allelic replacement of the sialic acid capsule polymerase.

Table 4 further provides a list of meningococcal strains in which capsule switching has been observed. Strains of all serogroups, i.e., A, B, C, Y and W-135, have been transformed and subject to gene, or operon, recombination.

TABLE 4

Meningococcal Strains Exhibiting Capsule Switching Recombination.

| Strain | Phenotype |
|---|---|
| NMB-43 | Mutant derivative of parental strain NMB (clinically isolated serogroup B *Neisseria meningitidis*). Contains Class I Tn916 insertion in the synD polysialyltransferase gene inactivating group B capsule production. Mutation has been mobilized into prototype strains of other serogroups as described below. |
| NMB-M7 | Mutant derivative of parental strain NMB. Contains Class I Tn916 insertion in the synX capsule biosynthesis gene inactivating group B capsule production. Mutation has been mobilized into prototype strains of other serogroups as described below. |
| Fam18-43 | Serogroup C prototype strain transformed with 43 mutation from NMB-43. |
| Fam18-M7 | Serogroup C prototype strain transformed with M7 mutation from NMB-M7. |
| 1205 | Serogroup C, ET301 strain isolated from Oregon outbreak. |
| 1205-43 | Serogroup C, ET301 strain isolated from Oregon outbreak transformed with the 43 mutation from NMB-43. |
| 1205-43CC | Capsule conversion derivative of strain 1205-43 in which the transposon insertion has precisely excised from the transformed synD gene resulting in the production of serogroup B capsule. |
| 1205-M7 | Serogroup C, ET301 strain isolated from Oregon outbreak transformed with the M7 mutation from NMB-M7. |
| 1198 | Serogroup C, ET301 strain isolated from Oregon outbreak. |
| 1204 | Serogroup C, ET301 strain isolated from Oregon outbreak. |
| F8229 | Serogroup A prototype strain obtained from the CDC and originally isolated on the African Continent. Encapsulated. |
| F8239 | Unencapsulated variant of the same serogroup A prototype strain. |
| F8239-43 | Serogroup A prototype strain obtained from the CDC and originally isolated on the African Continent transformed with the 43 mutation from NMB-43. |
| F8239-M7 | Serogroup A prototype strain obtained from the CDC and originally isolated on the African Continent transformed with the M7 mutation from NMB-M7. |
| GA0929 | Serogroup Y prototype strain isolated as part of the Metropolitan Atlanta Active Surveillance Project. Encapsulated. |
| GA0929-43 | Serogroup Y prototype strain transformed with the 43 mutation from NMB-43. |
| GA0929-M7 | Serogroup Y prototype strain transformed with the M7 mutation from NMB-M7. |
| GA1002 | Serogroup W-135 prototype strain isolated as part of the Metropolitan Atlanta Active Surveillance Project. Encapsulated. |
| GA1002-43 | Serogroup W-135 prototype strain transformed with the 43 mutation from NMB-43. |
| GA1002-M7 | Serogroup W-135 prototype strain transformed with the M7 mutation from NMB-M7. |

This invention embodies the discovery of a general strategy by which meningococci and other encapsulated bacteria capable of causing epidemic outbreaks or endemic disease escape vaccine-induced or natural protective immunity. In view of this discovery, this invention provides multivalent vaccines effective against all major capsular serogroups which may be needed to control epidemics and possibly endemic disease.

Techniques are available for the generation of stable insertion mutations in *N. meningitidis* and other Neissetia species. Stephens and co-workers have described Tn916 mutagenesis of different neisserial species [Stephens et al. (1991) *Infect. Immun.* 59:4097–4102; Stephens et al. (1994) *Infect. Immun.* 62:2947–2952; Kathariou et al. (1990) *Mol. Microbiol.* 4:729–735]. Two types of insertion mutations occur: class I insertions appear to have an intact Tn916 element resulting from transposition of the transposon and class II insertions are characterized by deletion of part of the transposon with maintenance of the tetM element which confers tetracycline resistance. Insertions can be characterized in part with analysis of HaeIII-digested DNA in that Tn916 has no HaeIII sites, and the portion of the genome into which the transposon or tetracycline-resistance determining region has inserted by subcloning a HaeIII fragment with selection for antibiotic resistance. Flanking sequences can be used for sequence determination and/or for use in probe or primer for the isolation of the wild-type counterpart gene from the parental strain. Stable mutations can be generated, including, but not limited to, deletion mutations, insertion mutations or multiple point mutations, and this may be accomplished by techniques including but not limited to oligonucleotide site-directed mutagenesis, polymerase chain reaction mutagenesis techniques, restriction endonuclease cutting and religation with or without insertion of heterologous DNA as appropriate for the type of mutation being created, as well known to one of ordinary skill in the art. The skilled artisan is capable of generating such alternate mutants using ordinary skill in the art; in particular, the DNA sequence information provided herein (e.g., serogroup C synE (SEQ ID NO:2), serogroup Y synF (SEQ ID NO:3), serogroup W-135 synF (SEQ ID NO:4) and serogroup A orf1–orf4 (SEQ ID NO:8) can be employed in mutagenic strategies. The sequence information provided can be used to produce multiple mutations. It is preferred that where a transposon is used, that the resulting mutation itself is not an insertion which is further transposable.

The skilled artisan recognizes that other neisserial (and certain *H. influenzae*) strains can express a non-isogeneic serogroup capsular polysaccharide as expressed by the recombinant characteristics of *N. meningitidis* B-301 strains 1070 and 1069, for example. The distinguishing characteristics of these recombinant strains (e.g., B-301 1070 and 1069) are (a) the presence of a capsular polysaccharide enzyme gene specific to serogroup C *N. meningitidis* strains (C synE) encoding ($\alpha$2→8)-linked polysialyltransferase in an otherwise isogeneic (serogroup B) capsule biosynthesis operon and (b) immunological resistance to a vaccine based on solely serogroup B capsule polysaccharide epitopes (e.g., ($\alpha$2→8)-linked polysialic acids). A recombinant strain of *N. meningitidis* can be identified not only by the presence of a gene encoding a capsular polysaccharide of a different serotype, but also by specific binding to a monoclonal antibody to a capsular polysaccharide of a non-isogeneic serogroup. In view of the similarity of the basic structures of capsular polysaccharide molecules of the meningococci, gonococci and certain *H. influenzae* strains, the skilled artisan understands that an antibody, particularly a monoclonal antibody which is specific for a particular epitope, directed to a particular capsular polysaccharide of a meningococcal specific serogroup strain can be used to screen other encapsulated bacterial strains for the presence of the epitopes recognized by that (monoclonal) antibody.

A polynucleotide or fragment thereof is substantially homologous (or substantially similar) to another polynucleotide if, when optimally aligned (with appropriate nucleotide insertions or deletions) with another polynucleotide, there is nucleotide sequence identity for approximately 80% of the nucleotide bases, usually approximately 90%, more preferably about 95% to 100% of the nucleotide bases.

Alternatively, substantial homology (or similarity) exists when a polynucleotide or fragment thereof will hybridize to another polynucleotide under selective or stringent hybridization conditions. Selectivity of hybridization exists under stringent hybridization conditions which allow one to distinguish the target polynucleotide of interest from other polynucleotides. Typically, selective hybridization will occur when there is approximately 75% similarity over a stretch of about 14 nucleotides, preferably approximately 80% similarity, more preferably approximately 85% similarity, and most preferably approximately 90% similarity. See Kanehisa (1984) *Nucl. Acids Res.,* 12:203–213. The length of homology comparison, as described, may be over longer stretches, and in certain embodiments will often be over a stretch of about 17 to 20 nucleotides, preferably 21 to 25 nucleotides, more preferably 26 to 35 nucleotides, and more preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1 M, typically less than 500 mM, and preferably less than 200 mM. However, the combination of parameters is much more important than the measure of any single parameter (Wetmur and Davidson (1968) *J. Mol. Biol.* 31, 349–370). Reaction conditions which favor the detection of well-matched hybrids involve high temperatures of hybridization (65–68 C. in aqueous solutions and 42 C. in 50% formamide) combined with washing at high temperatures (5–25 C. below $T_m$) and at low salt concentrations (0.1×SSC).

An isolated or substantially pure polynucleotide is a polynucleotide which is substantially separated from other polynucleotide sequences which naturally accompany a native sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate hybridizing, homologous coding sequences. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a proteinase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli,* although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.,* 22: 1859–1862 or the triester method according to Matteuci et al. (1981) *J. Am. Chem. Soc.* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology,* Greene Publishing and Wiley Interscience, New York; and Metzger et al. (1988) *Nature,* 334: 31–36. Many useful vectors for expression in bacteria, yeast, mammalian, insect, plant or other cells are well known in the art and may be obtained such vendors as Stratagene, New England Biolabs, Promega Biotech, and others. In addition, the construct may bejoined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the capsule polysaccharide biosynthetic gene (or mutant gene) sequence of interest can be introduced into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with capsular polysaccharide-related polynucleotides of the present invention in compatible vectors or other expression vehicles and culturing such transformed host cells under conditions suitable to attain expression of the desired capsular polysaccharide structure. The derivative polysaccharide may then be recovered from the host cell and purified. For example, it may be possible to create recombinant polysialyltransferases that could be over-expressed, purified, and used in vitro reactions to create capsular polysaccharide materials of substantial purity. Substantially pure capsular polysaccharides can be used as hybridization probes or in the preparation of vaccines.

When it is desired to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, a translation initiation codon (ATG) and the codons for the first amino acids of the mature protein. The oligonucleotide for site-directed mutagenesis at the 3' end of the coding sequence includes nucleotides encoding the carboxyterminal amino acids of the protein, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87: 2800–2804, as modified for use with PCR.

In another embodiment, polyclonal and/or monoclonal antibodies capable of specifically binding to a particular serogroup capsular polysaccharide or fragments thereof are provided. The term antibody is used to refer both to a homogenous molecular entity and a mixture such as a serum product made up of a plurality of different molecular entities. Monoclonal or polyclonal antibodies, preferably monoclonal, specifically reacting with capsular polysaccharide of a particular serogroup of interest may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York; and Ausubel et al. (1987) supra. Also, recombinant immunoglobulins may be produced by methods known in the art, including but not limited to the methods described in U.S. Pat. No. 4,816,567, incorporated by reference herein. Monoclonal antibodies with affinities of $10^8$ $M^{-1}$, preferably $10^9$ to $10^{10}$ or more are preferred.

Antibodies generated against a specific serogroup capsular polysaccharide of interest are useful, for example, as probes for screening DNA expression libraries or for detecting the presence of neisserial strains in a test sample. Antigens can be synthesized and conjugated to a suitable carrier protein (e.g., bovine serum albumin or keyhole limpet hemocyanin) for use in vaccines or in raising specific antibodies. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescentagents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for a particular serogroup capsular polysaccharide and capable of inhibiting adherence of neisserial and/or hemophilus cells expressing the particular capsular polysaccharide to host tissue are be useful in preventing disease resulting from neisserial and/or hemophilus infection. Such antibodies can be obtained by the methods described above.

Compositions and immunogenic preparations including vaccine compositions comprising substantially purified serogroup-specific capsular polysaccharides and a suitable carrier therefor are provided. Alternatively, antigens can be synthesized and conjugated to a suitable carrier protein (e.g., bovine serum albumin or keyhole limpet hemocyanin) for use in vaccines or in raising antibody specific for capsular polysaccharide-expressing neisserial and/or *H. influenzae* strains. Immunogenic compositions are those which result in specific antibody production when injected into a human or an animal. Such immunogenic compositions are useful, for example, in immunizing a humans, against infection by neisserial and hemophilus pathogenic strains. The immunogenic preparations comprise an immunogenic amount of, as specifically exemplified, at least one serogroup-specific capsular polysaccharide preparation derived from one serogroup strain of *N. meningitidis* and a suitable carrier. Alternatively, the immunogenic composition can comprise cells of at least one of the specifically exemplified recombinant *N. meningitidis* strains and a suitable carrier. It is understood by one of ordinary skill in the art that other, functionally equivalent, recombinant strains of *N. meningitidis,* for example, B-301 strain 1070, can be produced by the introduction of the cloned DNA containing the insertion mutations responsible for a C serogroup characteristic. It is also within the scope of the present invention and readily within the grasp of the ordinary skilled artisan to generate other types of genetically stable mutations in the capsular polysaccharide enzyme genes of *N. meningitidis* and/or *N. gonorrhoeae* or *H. influenzae.* Such immunogenic compositions (or vaccines) are useful, for example, in immunizing an animal, especially humans, against neisserial disease resulting from infection by pathogenic neisserial species, particularly *Neisseria meningitidis* and *Neisseria gonorrhoeae.* Such immunogenic compositions can also elicit the production of antibodies which will cross react with capsular polysaccharides of, for example, *Hemophilus influenzae* strains expressing epitopes in common with those of the starting *N. meningitidis* strain(s). The immunogenic preparations comprise an immunogenic amount of an isogeneic or non-isogeneic serogroup capsular polysaccharide from a strain of *N. meningitidis* or *N. gonorrhoeae,* or an immunogenic fragment thereof, or of cells of one or more strains of Neisseria which express a specific serogroup capsular polysaccharide. Such immunogenic compositions advantageously further comprise capsular polysaccharides or neisserial cells of two or more other serological types, including, but not limited to, any known to the art, among which are serogroups A, B, C, D, E, H, I, K, L, W-135, X Y and Z [Apicella, M. (1995) *Neisseria meningitidis,* in *Principles and Practice of Infectious Disease* (4th edition), Eds. G. L. Mandell, J. E. Bennett and R. Dolin, Churchill Livingstone Inc., p. 1896]. It is understood that where whole cells are formulated into the immunogenic composition, the cells are preferably inactivated, especially if the cells are of a virulent strain. Such immunogenic compositions may comprise one or more additional capsular polysaccharide preparations, or another protein or other immunogenic cellular component. By "immunogenic amount" is meant an amount capable of eliciting the production of antibodies directed against neisserial capsular polysaccharides, including but not limited to those of exemplified *N. meningitidis* in an animal or human to which the vaccine or immunogenic composition has been administered.

Immunogenic carriers may be used to enhance the immunogenicity of the capsular polysaccharides. Such carriers include but are not limited to proteins and polysaccharides, liposomes, and bacterial cells and membranes. Protein carriers may be joined to the capsular polysaccharide molecules to form fusion proteins by recombinant or synthetic means or by chemical coupling. Useful carriers and means of coupling such carriers to polypeptide antigens are known in the art. The art knows how to administer immunogenic compositions so as to generate protective immunity on the mucosal surfaces of the upper respiratory system, especially the mucosal epithelium of the nasopharynx, where immunity specific for *N. meningitidis* and for the remainder of the respiratory system, particularly for *H. influenzae,* and for the epithelial surfaces of the genito-urinary tract, particularly for *N. gonorrhoeae,* is most helpful.

The immunogenic compositions may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Serogroup-specific capsular polysaccharides and cells producing capsular polysaccharides and/or fragments thereof may be formulated into immunogenic compositions as neutral or salt forms. Preferably, when cells are used they are of avirulent strains, or the cells are killed before use. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic capsular polysaccharide preparations (or peptide antigens related thereto) compositions are administered in a manner compatible with the dosage formulation, and in such amount as will be prophylactically and/or therapeutically effective. The quantity to be administered, which is generally in the range of about 100 to 1,000 μg of protein per dose, more generally in the range of about 5 to 500 μg of protein per dose, depends on the subject to be treated, the capacity of the individual's immune system to synthesize antibodies, and the degree of protection desired. Precise amounts of the active ingredient required to be administered may depend on the judgment of the physician and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

All publications, patent applications and patents cited herein are incorporated by reference in the same extent as if each individual publication, patent application or patent were specifically and individually indicated to be incorporated by reference.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1

Bacterial Strains

Forty serogroup B and C ET-5 complex meningococcal isolates recovered from Oregon, Washington State and California in 1994 and 1995 were used in these studies. In addition, meningococcal strains GA0078 (serogroup C GA0290[C]), NMB (B), C114 (B), M986 (B), 2996, (B), KB (B), 269B (B), FAM18 (C), 6083 (W-135), GA0929 (Y), F8229 (A), F8239 (A), NM-44/76 (B), GA1002 (W-135), *N. gonorrhoeae* strain FA19; and *N. lactamica* and other commensal Neisseria spp. were also used (as specified in Swartley et al. (1994) *J. Bacteriol.* 1530–1534 and McAllister et al. (1993) *Mol. Microbiol.* 13–23).

Serogroup A meningococcal strains F8229 and F8239 were originally isolated during an outbreak in Nairobi, Kenya in 1989 and were provided by the Centers for Disease Control and Prevention, Atlanta, Ga. Strain F8229 (CDC #1750) is encapsulated and was clinically isolated from the cerebrospinal fluid of a patient. Strain F8239 (CDC #16N3) is an unencapsulated variant originally isolated as a serogroup A strain from the pharnyx of an asymptomatic carrier. These strains belong to clonal group III-1 and are closely related to strains that have caused recurrent epidemics in Saudi Arabia, Chad and Ethiopia (and other parts of Africa). F8227ORF1Ω, F8229OF2Ω, F8229ORF2apha3, F8229ORF3Ω, and F8229ORF4Ω are serogroup A mutants created through insertional mutagenesis.

Meningococcal strain NMB (CDC #8201085) is a serogroup B (NT:P1.2,5:L3,7.9) strain originally isolated from the cerebrospinal fluid of a patient with meningococcal *meningitis* in Pennsylvania in 1982 (Stephens, D. S. et al., "Insertion of Tn916 in *Neisseria meningitis* resulting in loss of group B capsular polysacchride [1991] *Infect. Immun.* 59:4097–4102). *Escherichia coli* strain αInvF' (Invitrogen) was used as the host strain for all cloned PCR products and recombinant plasmids created during these studies. Plasmid pHP45 (Prentki, P. and Krisch, H. M., "In vitro insertional mutagenesis with a selectable DNA fragment [1984] *Gene* 29:303–313) was the source of the spectinomycin resistant Ω-fragments used for polar gene mutagenesis and plasmid pUC18K (Menard, R. et al., "Nonpolar mutagenesis of the ipa genes defines IpaB, IpaC and IpaD as effectors of *Shigella flexneri* entry into epithelial cells," [1993] *J. Bacteriol.* 175:5899–5906) was the source of the apha-3 kanamycin resistance cassette used for the non-polar mutagenesis.

Example 2

Growth Conditions

Meningococcal strains were grown on GC base agar (Difco) or in GC broth (38) at 37° C. with 3.5% $CO_2$. Minimal media with an without supplements were prepared as described previously [Swartley et al. (1994) *J. Bacteriol.* 176:1530–1534]. *E. coli* strains were grown on Luria-Bertani agar plates (Bethesda Research Laboratories) or in Luria-Bertani broth at 37° C. *E. coil* strain harboring putative lacZ transcriptional reporter gene constructs were screened on MacConkey agar plates (Difco). Antibiotics were used at the following concentrations: tetracycline (5 μg/ml), spectinomycin (100 μg/ml), kanamycin (60 mg/ml), and ampicillin (100 mg/ml).

Example 3
Molecular Epidemiology

Multiple enzyme electrophoretic (ET) typing was carried out according to the protocol described in Reeves et al. (1995), *Emerging Infect. Dis.* 2:53–54, and pulsed field gel electrophoresis (PFGE) was performed as described in Bygraves et al. (1992) *J. Gen. Microbiol.* 138:523–531. Specific enzyme types (e.g., ET-301) were designated by the Centers for Disease Control Meningococcal Reference Laboratory. Serotyping of meningococcal strains was done as described in Wedege et al. (1990) *J. Med. Microbiol.* 31:195–201, with the following modifications. The serotyping procedure was modified to grow meningococci on brain heart infusion agar (BHI) (Difco) supplemented with 1% horse serum (Gibco), and to use a higher concentration of cells (cell density 1.0 at $OD_{600}$), different blocking buffer (PBS+0.1% Tween-20) and shorter primary antibody incubation (2.5 h).

Example 4
Transposon Mutagenesis

Tn916 is introduced into a strain of *N. meningitidis* of known serogroup by transformation as described [Kathariou et al. (1990) *Mol. Microbiol.* 4:729–735], and the presence of the transposon was selected in solid medium with tetracycline. Preferably, the mutants isolated are the result of Class I insertions as described hereinabove.

The genetic stability during growth and laboratory passage for each Tn916 insertion mutant strain was tested. Only mutants having the phenotype of drug resistance and the presence of a non-isogeneic capsular polysaccharide gene as revealed by nucleotide sequence analysis were selected. Expression of a non-isogeneic serogroup marker is the result of homologous recombination via the DNA flanking the Tn916-derived portion of the DNA transformed into the parental strain.

Example 5
Capsular Polysaccharide Preparations

Meningococcal capsular polysaccharides are prepared according to the procedures of Gotschlich et al. (1969) *J. Exp. Med.* 129:1349–1365. Methods are disclosed for the preparation and analyses of immunological properties of serogroup A, B and C meningococcal polysaccharides.

Example 6
SDS Page Analysis

Tricine-SDS polyacrylamide gels (14% acrylamide) were prepared as previously outlined [Schagger and von Jagow (1987) *Anal. Biochem.* 166:368–379] using the mini-Protean Protean II apparatus (BioRad, Hercules, Calif.). Each sample is heated to 100° C. for four minutes before loading. About 125 ng total protein is loaded per lane. The sample is electrophoresed at 30 V through the stacking gel and at 95 V through the separating gel. Prestained low molecular weight markers (Boehringer Mannheim, Indianapolis, Ind.) were used. Bands were visualized using the silver staining method as described in Hitchcock and Brown (1983) supra.

Example 7
Creation of Intergenic Region lacZ Transcriptional Reporter Gene Constructs A 250-bp product containing the entire 134-bp intergenic region was PCR amplified and the produce was cloned in both orientations into the PCR product cloning vector pCR2000, using the TA PCR product cloning system (Invitrogen), thereby creating plasmids pCRINT1 and pCRINT2. The cloned intergenic region was then liberated from pCRINT1 and pCRINT2 with KpnI and cloned into KpnI-linearized, shrimp alkaline phosphatase (United States Biochemicals)-treated pEU730, a low-copy-number, promoterless, lacZ transcriptional fusion vector [Froehlich et al. (1991) *Gene* 108:99–101]. The ligations were then transformed into *E. coli* MC4100 and plated on selective MacConkey agar. Strain MC4100 was used because its lactose utilization operon has been deleted and it forms white colonies on MacConkey media. We screened for transcriptionally active spectinomycin-resistant transformants (red colonies on MacConkey agar), indicating that we had cloned the ctrA promoter and the synX promoter of the intergenic region behind the lacZ gene of pEU730, thereby creating the target plasmids pEU730C and pEU730S, respectively. The promoter activities of these clones were measured by β-galactosidase assays in Miller units as described below.

Example 8
β-Galactosidase Assays

To investigate the possible promoter activities of cloned intergenic region constructs, we performed β-galactosidase assays with *E. coli* (Sambrook et al. (1989) *Molecular cloning: a laboratory manual,* Cold Spring Harbor Laboratory, Cold Spring Harbor, N.Y.). Briefly, *E. coli* MC4100 strains harboring test and control constructs were grown to mid-log phase in complete liquid media. The cells were then pelleted and resuspended in a salt solution (1 liter, 5×recipe: 64 g of $Na_2HPO_4.7H_2O$, 15 g of $KH_2PO_4$, 2.5 g of NaCl, 5.0 g of $NH_4Cl$) and the $A_{600}$ was recorded. The cells were diluted in Z buffer (0.06 M $Na_2HPO_4$, 0.04 M $NaH_2PO_4$, 0.01 M KCl, 0.001 M $MgSO_4.7H_2O$, 0.05 M β-mercaptoethanol [pH 7.0]), containing 0.1% SDS and chloroform. The diluted cells were then vortexed briefly, incubated at 28° C. for 10 minutes, and then vortexed again. A 0.2 ml ONPG (O-nitrophenyl-β-D-galactopyranoside) solution (4 mg of ONPG per mg in the aforementioned salt solution) was added to the lysed cells, and the time until a yellow color developed was measured. The reaction was then terminated by the addition of 1 M $Na_2CO_3$. The $A_{420}$ and the $A_{550}$ of the stopped reaction mixture were recorded, and Miller units were then calculated by the following formula: $1,000 \times [A_{420} - (1.75 \times A_{550})]$/time in minutes × volume of cells used in milliliters × $A_{600}$.

Example 9
DNA Sequencing

For determination of the sequence flanking the Tn916-derived insertion, the fragment of DNA comprising the insertion is cloned into a suitable plasmid vector, for example, after HaeIII digestion of chromosomal DNA. Double-stranded DNA was subcloned and sequenced by the dideoxy chain termination method [Sanger et al. (1977) *Proc. Natl. Acad. Sci. USA* 74:5463–5467], for example, using sequencing kits purchased from United States Biochemical Corporation (Cleveland, Ohio). Oligonucleotide primers for sequencing reactions are synthesized by the phosphoramidite method with an Applied Biosystems model 394 automated DNA synthesizer (Applied Biosystems, Foster City, Calif.), purified by PAGE and desalted on Sep-Pak (Millipore Corp., Beverly, Mass.) using standard protocols.

Example 10
Analytical Methods of Molecular Biology

The colony immunoblot screening was performed as described by Kahler et al. (1996) *J. Bacteriol.* 178:1265–1273. PCR, Southern DNA hybridization and DNA sequencing techniques were performed as previously described [Swartley et al. (1993) *Mol. Microbiol.* 10:361–369]. Automated sequencing using an ABI model 377 automated DNA sequencing system (Applied Biosystems, Foster City, Calif.) was performed on some PCR templates. Oligonucleotide primers used for PCR, sequencing and construction of Southern probes were:

5' ctrA: 5'GTGTGGAAGTTTAATTGTAGGATG-3' [SEQ ID NO:13;

3' ctrA: 5'-CCACCACCAAACAATACTGCCG-3' [SEQ ID NO:14];

5' synX: 5'-GCAATACCATTACGTTTATCTCTC-3' [SEQ ID NO:151];

3'synX: 5'-GTTTCAGGATTGTTGATTACTTCAGC-3' [SEQ ID NO:16];

5'synB: 5'-GTCCTACGCCCTGCAGAGCTGG-3' [SEQ ID NO:17];

3' synB: 5'-CATTAGGCCTAAATGCCTGAGG-3' [SEQ ID NO:18];

5' synC: 5'-GCTGAAGTTGTTAAACATCAAACAC-3' [SEQ ID NO:19];

3' synC: 5'-GCTACGACAGATGCAAAGGCG-3' [SEQ ID NO:20];

5' synD: 5'-AGAGGATTGGCTATTACATATAGC-3' [SEQ ID NO:21];

3' synD: 5'AGCTCTGTTGTCGATTACTCTCC-3' [SEQ ID NO:22];

5' FKBP: 5'-CATTACACAGGTTGGCTGGAAGACGG-3' [SEQ ID NO:23];

3' FKBP: 5'-GCAGCTCGACTTCAAATATCAAAGTGGC-3' [SEQ ID NO:24];

5' recA: 5'-GCCAGCAGGAAGAAAACCTCG-3' [SEQ ID NO:25];

3' recA: 5'-GCCGTTGTAGCTGTACCACGC-3' [SEQ ID NO:26];

5' ctrA-synX: 5'-CACCACCAAACAATACTGCC-3' [SEQ ID NO:27];

3' ctrA-synX: 5'-GCTTGTTCATTTGCTACCAAGTGG-3' [SEQ ID NO:28];

5' galE: 5'-CCAGCATCAATATCCTGCCACG-3' [SEQ ID NO:29];

3' galE: 5'-CCATCATTTGTGCAAGGCTGCG-3' [SEQ ID NO:30].

Nucleotide sequences were analyzed using either the DNASTAR (DNASTAR, Inc.) sequence analysis software or the Genetics Computer Group (GCG) Sequence Analysis Software Package, Version 7.3.1 UNIX (Devereux et al. (1984) *Nucl. Acids Res.* 12:387–395). Plate transformations of meningococcal strains were performed as described in Swartley et al. (1993) *Mol. Microbiol.* 10:361–369.

For primer extension, the avian myeloblastosis virus reverse transcriptase (RT) primer extension system (Promega) was used according to the manufacturer's directions. Briefly, an antisense primer predicted to bind approximately 100 nucleotides from the 5' end of the mRNA transcript was 5' end labeled with [$\gamma$-$^{32}$P]ATP and polynucleotide kinase. The primer extension reaction mixture contained 100 fmol of the labeled primer, 40 $\mu$g of whole-cell RNA, and 1 U of avian myeloblastosis virus RT in an appropriate buffer. The labeled primer directed cDNA synthesis of the mRNA transcript with avian myeloblastosis virus RT. cDNA synthesis continued to the 5' end of the RNA transcript, where it terminated, resulting in a labeled cDNA molecule of precisely defined length. The primer extension reaction mixtures, along with a standard dideoxy DNA sequencing reaction mixture catalyzed by the extension primer on control template DNA, were then run on an 8% polyacrylamide sequencing gel in order to define the precise nucleotide start site of the cDNA product. After electrophoresis, the gel was harvested and autoradiographed with X-ray film.

The following primers were used for primer extensions as described above. The 3' end of primer LJ6 (5'-CATCCTACAATTAAACTTCCACAC-3' [SEQ ID NO:31]) anneals 44 nucleotides downstream of the ctrA start codon (GTG) and was used to define the ctrA transcriptional start site. The 3' end of primer JS56 (5'-GAATACTAATTATACTCTACGTACTC-3' [SEQ ID NO:32]) anneals 72 nucleotides upstream of the synX start codon (ATG) and was used to define the synX transcriptional start site.

Example 11

Nucleic Acid Purification

Chromosomal DNA was isolated using the procedure described by DiLella and Woo (DiLella, A. G., and Woo, S. L. C., "Cloning large segments of genomic DNA using cosmid vectors," [1987] *Meth. Enzymol.* 152:199–212). RNA obtained from whole bacterial cells was prepared using a modification of the method of Baker et al. (1968) *Proc. Natl. Acad. Sci. USA* 60:313–320, and Swartley et al., (1996) *J. Bacteriol.* 178:4052–4059).

Example 12

Standard PCR and Single-Specific-Primer (SSP)-PCR

Standard PCR reactions were performed as described by Swartley et al. (1993) *Mol. Microbiol.* 10:299–310. Oligonucleotide primers used are given in Table 1. Amplified products were visualized by 1.2% agarose gel electrophoresis and UV detection after ethidium bromide staining. PCR products were purified by passage through Qiaquick PCR-purification Spin Columns (Qiagen) prior to further manipulations. Chromosome walking via single-specific-primer (SSP)-PCR was performed using the technique described by Shyamala and Ames (1989) *Gene* 84:1–8).

Example 13

Primer Extension and Reverse Transcriptase (RT)-PCR

The AMV Reverse Transcriptase Primer Extension System (Promega) was carried out according to the manufacturer's directions. A reverse transcriptase (RT)-PCR assay was carried out as previously described (Swartley et al., [1996] supra).

Example 14

Colony PCR

A single colony from a plated culture was collected using a sterile loop and resuspended in 20 $\mu$l of sterile distilled water. The colony suspension was then subjected to two rounds of freeze-thawing using a dry ice-ethanol bath and a 37° C. water bath. One microliter of the freeze-thaw mixture was then used as template in standard PCR.

Example 15

Cloning of PCR Products

DNA products amplified using standard PCR or SSP-PCR were cloned using the TA Cloning® Kit (Invitrogen) or the pGEM®-T Vector System (Promega).

Example 16
Nucleotide Sequencing

Purified plasmid DNA and PCR products were sequenced by both manual and automated means. Oligonucleotide primers used are shown in Table 2. For manual sequencing the AmpliTaq Cycle Sequencing Kit (Perkin Elmer) was used according to the manufacturer's directions. Automated DNA sequencing was performed using the Prism Dye-Termination Cycle Sequencing Kit (Applied Biosystems) and completed reactions were run on an Applied Biosystems Model 377 Automated DNA Sequencer.

Example 17
Computer Sequence Analysis

Nucleotide and amino acid sequence analysis was performed using either the DNASTAR sequence analysis package (DNASTAR, Inc.) or the Genetics Computer Group (GCG) sequence analysis software package version 7.3.1-UNIX (Devereaux et al. [1984] Nucl. Acids Res. 12:387–395).

Example 18
Polar and Nonpolar Insertional Mutagenesis

Polar mutagenesis of defined genes was conducted by insertion of anΩ-spectinomycin resistance cassette derived from pHP45 (Prentki, P. and Krisch, H. M., "In vitro insertional mutagenesis with a selectable DNA fragment," [1984] Gene 29:303–313). Briefly, the genetic region to be interrupted was amplified by PCR from chromosomal DNA and then cloned into E. coli. The plasmid containing the cloned PCR product was then linearized at a unique, blunt-ended restriction site present in the insert. A blunt SmaI fragment derived from pHP45, containing the entire Ω-spectinomycin resistance cassette, was then ligated into the cloned product and transformed into E. coli with selection for spectinomycin resistance. Putative transformants were checked by colony PCR to confirm assembly of appropriate constructs. Plasmid DNA was prepared from confirmed transformants and used to transform serogroup A strain F8229 with selection for spectinomycin resistance. Putative meningococcal transformants were checked by colony PCR and Southern DNA hybridization to confirm acquisition of the polar Ω-insertion mutation by homologous recombination. Primers JS102 and JS103 were used to amplify a 600 bp PCR fragment from the 5' end of the F8229 ORF1 which was subsequently cloned in E. coli. This product contained a unique StuI restriction site located 356 bp downstream of the predicted ORF1 start codon. A SmaI fragment from pHP45, encoding the Ω-spectinomycin resistance cassette, was inserted into the unique StuI site, and the resulting recombinant plasmid was used to transform wild-type serotype A strain F8229. Spectinomycin-resistant transformants were selected and acquisition of the Ω-insertion was confirmed by colony PCR and Southern hybridization.

The same approach was used to introduce Ω-spectinomycin resistance cassettes into ORF2, ORF3 and ORF4. To inactivate ORF2, a 451 bp DNA fragment derived from ORF2 was PCR amplified from strain F8229 using primers JS104 and JS105. An Ω-fragment was inserted into a unique HincII site present in the cloned PCR product (located 729 bp from the putative ORF2 start codon), and the resulting plasmid was transformed into strain F8229. Primers SE57 and SE61 were used to amplify an 858 bp product from ORF3, containing a unique Sspi site located 507 bp downstream of the ORF3 start codon. Again, an Ω-fragment was inserted into this cloning site, and the construct was transformed into F8229. Finally, a 765 bp product was amplified from ORF4 using primers SE63 and SE56. The unique SspI cloning site in this product was located 159 bp from the putative ORF4 start codon. An Ω-fragment was inserted into the cloning site, and the construct was transformed into F8229.

Nonpolar mutants were created using the same allelic exchange technique described above; however, instead of using a polar Ω-fragment, a non-polar aphA-3 kanamycin resistance cassette derived from pUC18K (Menard, R. et al., [1993] J. Bacteriol. 175:5899–5906) was inserted into the genetic region to be mutated. The orientation of the aphA-3 insertion was checked by colony PCR and direct DNA sequencing to ensure that the cassette was fused in frame to the downstream sequences.

Example 19
DNA Transformation Procedures

Serogroup A meningococcal strain F8229 was transformed using the semi-quantitative transformation assay of Janik et al. [1976] J. Clin. Microbiol. 4:71–81). Chemical transformation of E. coli was performed using the method described by Chung et al. (1989) Proc. Natl. Acad. Sci. USA 86:2172–2175).

Example 20
Southern DNA Hybridization

The Genius non-radioactive DNA labeling and detection system (Boerhinger Mannheim) was used. Specific DNA probes were PCR amplified, labeled with digoxigenin and used to probe Southern DNA blots according to the manufacturer's protocols.

Example 21
Capsule Quantitation by Colony Immunoblot and Whole Cell ELISA

Colony immunoblots were performed using the anti-serogroup A monoclonal antibody 14-1-A (generously provided by Dr. Wendell Zollinger, Walter Reed Army Institute of Research). Whole cell ELISA was performed using the method of Abdillahi and Poolman (1987) FEMS Microbiol. Lett. 48:367–371). Briefly, strains to be assayed were grown overnight on GC agar plates. Plate growth was then harvested and suspended in 5 ml of PBS containing 0.02% sodium aide. The cells were heat inactivated at 56 for 30 minutes, then adjusted to an $A_{650}$ of 0.1 and stored at 4° C. until needed. To perform the ELISA, 100 µl of the cell suspension was added to a flat-bottomed microtiter plate (NUNC Maxi-sorp or Poly-sorp) and evaporated overnight at 33° C. The plate was then washed three times with a 0.05% solution of Tween 80 in sterile water. One hundred microliters of monoclonal antibody 14-1-A (diluted 1:10,000 in PBS containing 0.01% Tween 80 and 0.3% Casamino acids) was added to each well and the plate was incubated at 33° C. for one hour. After a three-fold wash, 100 µl of goat anti-mouse IgA,G,M alkaline phosphatase conjugated antibody was added (diluted 1:10,000 in the above buffer) and incubated for 90 minutes at 33° C. The plate was washed three times, and 200 µl of substrate (1 mg p-nitrophenyl phosphate dissolved per ml of 0.5M diethanolamine buffer containing 0.5 mM $MgCl_2$, pH 9.8) was added and left to stand at room temperature for 20–45 minutes. The reaction was stopped by the addition of 50 µl 3N NaOH and the $A_{405}$ of each well was read using a BIO-TEK(BIO-TEK Instruments, Winoski, Vt.) model EL 312e automated plate reader.

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
        (A) LENGTH: 319 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:1:

```
GTCCGGAGAT AACCTATGGG TTAAACGCCC AGGCAATGGA GACTTCAGCG TCAACGAATA      60

TGAAACATTA TTTGGTAAGG TCGCTGCTTG CAATATTCGC AAAGGTGCTC AAATCAAAAA     120

AACTGATATT GAATAATGCT TATTAACTTA GTTACTTTAT TAACAGAGGA TTGGCTATTA     180

CATATAGCTA ATTCTCATTA ATTTTTAAGA GATACAATAA TGCTAAAGAA AATAAAAAAA     240

GCTCTTTTTC AGCCTAAAAA GTTTTTTCAA GATTCAATGT GGTTGACAAC ATCTCCATTT     300

TATCTTACCC CCCCACGTA                                                  319
```

(2) INFORMATION FOR SEQ ID NO:2:

(i) SEQUENCE CHARACTERISTICS:
        (A) LENGTH: 315 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:2:

```
GTCCGGAGAT AACCTATGGG TTAAACGCCC AGGCAATGGA GACTTCAGCG TCAACGAATA      60

TGAAACATTA TTTGGTAAGG TCGCTGCTTG CAATATTCGC AAAGGTGCTC AAATCAAAAA     120

AACTGATATT GAATAAAAAT CTATAAATTG ACTCAATTTA ATGATAATCG GCTGACTTTT     180

CAGTCGATTA TCATTAAAAA TATACGGAAA AACAAATGTT GCAGAAAATA AGAAAAGCTC     240

TCTTCCACCC AAAAAAATTC TTCCAAGATT CCCAGTGGTT TGCAACACCT TTATTTAGCA     300

GCTTCGCACC CAAAA                                                      315
```

(2) INFORMATION FOR SEQ ID NO:3:

(i) SEQUENCE CHARACTERISTICS:
        (A) LENGTH: 319 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:3:

```
GTCCGGAGAT AACCTATGGG TTAAACGCCC AGGCAATGGA GACTTCAGCG TCAACGAATA      60

TGAAACATTA TTTGGTAAGG TCGCTGCTTG CAATATTCGC AAAGGTGCTC AAATCAAAAA     120
```

```
AACTGATATT AGTTAATAAT AAAATAGATT AAGCTATTCT TAAATTCAGA ATATTGCTTA      180

TCTATATTAA AAATTTCTAA TTTTTAAGGT TCTGATTGAA ATCAGAACCT TATTTCAACT      240

ATTACTTTTT ACTCATAATC GAATTATATA CTTTAGGACT TTATAATATG GCTGTTATTA      300

TATTTGTTAA CGGAATTCG                                                   319
```

(2) INFORMATION FOR SEQ ID NO:4:

(i) SEQUENCE CHARACTERISTICS:
        (A) LENGTH: 319 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:4:

```
GTCCGGAGAT AACCTATGGG TTAAACGCCC AGGCAATGGA GACTTCAGCG TCAACGAATA       60

TGAAACATTA TTTGGTAAGG TCGCTGCTTG CAATATTCGC AAAGGTGCTC AAATCAAAAA      120

AACTGATATT AGTTAATAAT AAAATAGATT AAGCTATTCT TAAATTCAGA ATATTGCTTA      180

TCTATATTAA AAATTTCTAA TTTTTAAGGT TCTGATTGAA ATCAGAACCT TATTTCAACT      240

ATTACTTTTT ACTCATAATC GAATTATATA CTTTAGGACT TTATAATATG GCTGTTATTA      300

TATTTGTTAA CGGAATTCG                                                   319
```

(2) INFORMATION FOR SEQ ID NO:5:

(i) SEQUENCE CHARACTERISTICS:
        (A) LENGTH: 320 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "Consensus sequence generated from
            sequence comparison of SEQ ID NOs:1-4."

(iii) HYPOTHETICAL: YES (ix) FEATURE:
        (A) NAME/KEY: misc_feature
        (B) LOCATION: 141..142
        (D) OTHER INFORMATION: /note= "At nucleotide 141, N can be
            A, T, C or G or no nucleotide."

(ix) FEATURE:
        (A) NAME/KEY: misc_feature
        (B) LOCATION: 157..158
        (D) OTHER INFORMATION: /note= "At nucleotide 157, N can be
            A, T, C or G or no nucleotide."

(ix) FEATURE:
        (A) NAME/KEY: misc_feature
        (B) LOCATION: 182..183
        (D) OTHER INFORMATION: /note= "At nucleotides 182 and 183,
            N can be A, T C or G or no nucleotide."

(xi) SEQUENCE DESCRIPTION: SEQ ID NO:5:

```
GTCCGGAGAT AACCTATGGG TTAAACGCCC AGGCAATGGA GACTTCAGCG TCAACGAATA       60

TGAAACATTA TTTGGTAAGG TCGCTGCTTG CAATATTCGC AAAGGTGCTC AAATCAAAAA      120

AACTGATATT NNNTAATAAT NNANTANNTT ANNCNANTTN TTAANNNNNG ANTNNNNNTT      180

ANNTATANTN AANNNTNNTN ANTTTTAANG NNNTNANNNA ANNCNGAANN NNATNNNAAN      240
```

```
NNNTNNTTTT NACNCANAAN NGNNTTNTNN ANNTTNNNAN TNNNTNANAN NNCNNTTATT      300

NTATNTNTTN NCNNNANNNN                                                  320
```

(2) INFORMATION FOR SEQ ID NO:6:

(i) SEQUENCE CHARACTERISTICS:
        (A) LENGTH: 279 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:6:

```
GTCCGGAGAT AACCTATGGG TTAAACGCCC AGGCAATGGA GACTTCAGCG TCAACGAATA       60

TGAAACATTA TTTGGTAAGG TCGCTGCTTG CAATATTCGC AAAGGTGCTC AAATCAAAAA      120

AACTGATATT GAATAATGCT TATTAACTTA GTTACTTTAT TAACAGAGGA TTGGCTATTA      180

CATATAGCTA ATTCTCATTA ATTTTTAAGA GATACAATAA TGCTAAAGAA AATAAAAAAA      240

GCTCTTTTTC AGCCTAAAAA GTTTTTTCAA GATTCAATG                             279
```

(2) INFORMATION FOR SEQ ID NO:7:

(i) SEQUENCE CHARACTERISTICS:
        (A) LENGTH: 275 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:7:

```
GTCCGGAGAT AACCTATGGG TTAAACGCCC AGGCAATGGA GACTTCAGCG TCAACGAATA       60

TGAAACATTA TTTGGTAAAA TTGCTGCTTG TGATATTCGC AAAGGTGCTC AAATCAAAAA      120

AACTGATATC GAATAAAAAT CTATAAATTG ACTCAATTTA ATGATAATCG GCTGACTTTT      180

CAGTCGATTA TCATTAAAAA TATACGGAAA AACAAATGTT GCAGAAAATA AGAAAAGCTC      240

TCTTCCACCC AAAAAAATTC TTCCAAGATT CCCAG                                 275
```

(2) INFORMATION FOR SEQ ID NO:8:

(i) SEQUENCE CHARACTERISTICS:
        (A) LENGTH: 5064 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (ix) FEATURE:
        (A) NAME/KEY: CDS
        (B) LOCATION: 479..1597

(ix) FEATURE:
        (A) NAME/KEY: CDS
        (B) LOCATION: 1599..3236

(ix) FEATURE:
        (A) NAME/KEY: CDS
        (B) LOCATION: 3309..4052

(ix) FEATURE:
    (A) NAME/KEY: CDS
    (B) LOCATION: 4054..4917

(xi) SEQUENCE DESCRIPTION: SEQ ID NO:8:

```
AATACATCAC CAATATTTAG CGTACCGGTA GAAGCATAAC CATCGCCAAA CTGGGTAAAA      60

GACTGATTCA CCTGAGCTTT ATACAAAGAC TGCGCTACAG CATGATTGAC GTCAATCAAC     120

TCTACTTCAG GAATTTGAGC TTCAGACTGT TGCCCCAATG AGACAACTTT TTTTGCACTT     180

GGGCCAGAGG AGGGAATAGC ACTACATGCA CTTCCCAAAA TTAAAAAAGA AATTACAATA     240

CAAAACTTTA ACTTAAGCAT AAAATAAAAA ATCTCATTAA GTATGATTGT TTTTAAATAA     300

ATTTAAAACC TACCAGAGAT ACAATACCAC TTTATTTTGT AGAACACAAA CGTGTATAAT     360

ATATGACATA AACATCATCT TCGAAATAAT ATTGGGGCTT AGGAAGCAAA ATCATCAAAA     420

AACGTGATAA GCTCCTAATA TTTTTAACAC ATTACTATAT TACACATAGG ATATTCCA      478
```

| | | |
|---|---|---|
| ATG AAA GTC TTA ACC GTC TTT GGC ACT CGC CCT GAA GCT ATT AAA ATG<br>Met Lys Val Leu Thr Val Phe Gly Thr Arg Pro Glu Ala Ile Lys Met<br>1               5                  10                  15 | | 526 |
| GCG CCT GTA ATT CTA GAG TTA CAA AAA CAT AAC ACA ATT ACT TCA AAA<br>Ala Pro Val Ile Leu Glu Leu Gln Lys His Asn Thr Ile Thr Ser Lys<br>            20                  25                  30 | | 574 |
| GTT TGC ATT ACT GCA CAG CAT CGT GAA ATG CTA GAT CAG GTT TTG AGC<br>Val Cys Ile Thr Ala Gln His Arg Glu Met Leu Asp Gln Val Leu Ser<br>        35                  40                  45 | | 622 |
| CTA TTC GAA ATC AAA GCT GAT TAT GAT TTA AAT ATC ATG AAA CCC AAC<br>Leu Phe Glu Ile Lys Ala Asp Tyr Asp Leu Asn Ile Met Lys Pro Asn<br>    50                  55                  60 | | 670 |
| CAG AGC CTA CAA GAA ATC ACA ACA AAT ATC ATC TCA AGC CTT ACC GAT<br>Gln Ser Leu Gln Glu Ile Thr Thr Asn Ile Ile Ser Ser Leu Thr Asp<br>65                  70                  75                  80 | | 718 |
| GTT CTT GAA GAT TTC AAA CCT GAC TGC GTC CTT GCT CAC GGA GAC ACC<br>Val Leu Glu Asp Phe Lys Pro Asp Cys Val Leu Ala His Gly Asp Thr<br>                85                  90                  95 | | 766 |
| ACA ACA ACT TTT GCA GCT AGC CTT GCT GCA TTC TAT CAA AAA ATA CCT<br>Thr Thr Thr Phe Ala Ala Ser Leu Ala Ala Phe Tyr Gln Lys Ile Pro<br>            100                 105                 110 | | 814 |
| GTT GGC CAC ATT GAA GCA GGC CTG AGA ACT TAT AAT TTA TAC TCT CCT<br>Val Gly His Ile Glu Ala Gly Leu Arg Thr Tyr Asn Leu Tyr Ser Pro<br>        115                 120                 125 | | 862 |
| TGG CCA GAG GAA GCA AAT AGG CGT TTA ACA AGC GTT CTA AGC CAG TGG<br>Trp Pro Glu Glu Ala Asn Arg Arg Leu Thr Ser Val Leu Ser Gln Trp<br>    130                 135                 140 | | 910 |
| CAT TTT GCA CCT ACT GAA GAT TCT AAA AAT AAC TTA CTA TCT GAA TCA<br>His Phe Ala Pro Thr Glu Asp Ser Lys Asn Asn Leu Leu Ser Glu Ser<br>145                 150                 155                 160 | | 958 |
| ATA CCT TCT GAC AAA GTT ATT GTT ACT GGA AAT ACT GTC ATA GAT GCA<br>Ile Pro Ser Asp Lys Val Ile Val Thr Gly Asn Thr Val Ile Asp Ala<br>                165                 170                 175 | | 1006 |
| CTA ATG GTA TCT CTA GAA AAA CTA AAA ATA ACT ACA ATT AAA AAA CAA<br>Leu Met Val Ser Leu Glu Lys Leu Lys Ile Thr Thr Ile Lys Lys Gln<br>            180                 185                 190 | | 1054 |
| ATG GAA CAA GCT TTT CCA TTT ATT CAG GAC AAC TCT AAA GTA ATT TTA<br>Met Glu Gln Ala Phe Pro Phe Ile Gln Asp Asn Ser Lys Val Ile Leu<br>        195                 200                 205 | | 1102 |
| ATT ACC GCT CAT AGA AGA GAA AAT CAT GGG GAA GGT ATT AAA AAT ATT<br>Ile Thr Ala His Arg Arg Glu Asn His Gly Glu Gly Ile Lys Asn Ile<br>    210                 215                 220 | | 1150 |
| GGA CTT TCT ATC TTA GAA TTA GCT AAA AAA TAC CCA ACA TTC TCT TTT | | 1198 |

```
Gly Leu Ser Ile Leu Glu Leu Ala Lys Lys Tyr Pro Thr Phe Ser Phe
225                 230                 235                 240

GTG ATT CCG CTC CAT TTA AAT CCT AAC GTT AGA AAA CCA ATT CAA GAT     1246
Val Ile Pro Leu His Leu Asn Pro Asn Val Arg Lys Pro Ile Gln Asp
                245                 250                 255

TTA TTA TCC TCT GTG CAC AAT GTT CAT CTT ATT GAG CCA CAA GAA TAC     1294
Leu Leu Ser Ser Val His Asn Val His Leu Ile Glu Pro Gln Glu Tyr
                260                 265                 270

TTA CCA TTC GTA TAT TTA ATG TCT AAA AGC CAT ATA ATA TTA AGT GAT     1342
Leu Pro Phe Val Tyr Leu Met Ser Lys Ser His Ile Ile Leu Ser Asp
                275                 280                 285

TCA GGC GGC ATA CAA GAA GAA GCT CCA TCC CTA GGA AAA CCA GTT CTT     1390
Ser Gly Gly Ile Gln Glu Glu Ala Pro Ser Leu Gly Lys Pro Val Leu
290                 295                 300

GTA TTA AGA GAT ACT ACA GAA CGT CCT GAA GCT GTA GCT GCA GGA ACT     1438
Val Leu Arg Asp Thr Thr Glu Arg Pro Glu Ala Val Ala Ala Gly Thr
305                 310                 315                 320

GTA AAA TTA GTA GGT TCT GAA ACT CAA AAT ATT ATT GAG AGC TTT ACA     1486
Val Lys Leu Val Gly Ser Glu Thr Gln Asn Ile Ile Glu Ser Phe Thr
                325                 330                 335

CAA CTA ATT GAA TAC CCT GAA TAT TAT GAA AAA ATG GCT AAT ATT GAA     1534
Gln Leu Ile Glu Tyr Pro Glu Tyr Tyr Glu Lys Met Ala Asn Ile Glu
                340                 345                 350

AAC CCT TAC GGG ATA GGT AAT GCC TCA AAA ATC ATT GTA GAA ACT TTA     1582
Asn Pro Tyr Gly Ile Gly Asn Ala Ser Lys Ile Ile Val Glu Thr Leu
                355                 360                 365

TTA AAG AAT AGA TAA A ATG TTT ATA CTT AAT AAC AGA AAA TGG CGT      1628
Leu Lys Asn Arg  *   Met Phe Ile Leu Asn Asn Arg Lys Trp Arg
370                   1               5                   10

AAA CTT AAA AGA GAC CCT AGC GCT TTC TTT CGA GAT AGT AAA TTT AAC    1676
Lys Leu Lys Arg Asp Pro Ser Ala Phe Phe Arg Asp Ser Lys Phe Asn
                15                  20                  25

TTT TTA AGA TAT TTT TCT GCT AAA AAA TTT GCA AAG AAT TTT AAA AAT    1724
Phe Leu Arg Tyr Phe Ser Ala Lys Lys Phe Ala Lys Asn Phe Lys Asn
                30                  35                  40

TCA TCA CAT ATC CAT AAA ACT AAT ATA AGT AAA GCT CAA TCA AAT ATT    1772
Ser Ser His Ile His Lys Thr Asn Ile Ser Lys Ala Gln Ser Asn Ile
                45                  50                  55

TCT TCA ACC TTA AAA GAA AAT CGG AAA CAA GAT ATG TTA ATT CCT ATT    1820
Ser Ser Thr Leu Lys Glu Asn Arg Lys Gln Asp Met Leu Ile Pro Ile
60                  65                  70

AAT TTT TTT AAT TTT GAA TAT ATA GTT AAA AAA CTT AAC AAT CAA AAC    1868
Asn Phe Phe Asn Phe Glu Tyr Ile Val Lys Lys Leu Asn Asn Gln Asn
75                  80                  85                  90

GCA ATA GGT GTA TAT ATT CTT CCT TCT AAT CTT ACT CTT AAG CCT GCA    1916
Ala Ile Gly Val Tyr Ile Leu Pro Ser Asn Leu Thr Leu Lys Pro Ala
                95                  100                 105

TTA TGT ATT CTA GAA TCA CAT AAA GAA GAC TTT TTA AAT AAA TTT CTT    1964
Leu Cys Ile Leu Glu Ser His Lys Glu Asp Phe Leu Asn Lys Phe Leu
                110                 115                 120

CTT ACT ATT TCC TCT GAA AAT TTA AAG CTT CAA TAC AAA TTT AAT GGA    2012
Leu Thr Ile Ser Ser Glu Asn Leu Lys Leu Gln Tyr Lys Phe Asn Gly
                125                 130                 135

CAA ATA AAA AAT CCT AAG TCC GTA AAT GAA ATT TGG ACA GAT TTA TTT    2060
Gln Ile Lys Asn Pro Lys Ser Val Asn Glu Ile Trp Thr Asp Leu Phe
                140                 145                 150

AGC ATT GCT CAT GTT GAC ATG AAA CTC AGC ACA GAT AGA ACT TTA AGT    2108
Ser Ile Ala His Val Asp Met Lys Leu Ser Thr Asp Arg Thr Leu Ser
155                 160                 165                 170
```

```
TCA TCT ATA TCT CAA TTT TGG TTC AGA TTA GAG TTC TGT AAA GAA GAT    2156
Ser Ser Ile Ser Gln Phe Trp Phe Arg Leu Glu Phe Cys Lys Glu Asp
            175                 180                 185

AAG GAT TTT ATC TTA TTT TCT ACA GCT AAC AGA TAT TCT AGA AAA CTT    2204
Lys Asp Phe Ile Leu Phe Ser Thr Ala Asn Arg Tyr Ser Arg Lys Leu
            190                 195                 200

TGG AAG CAC TCT ATT AAA AAT AAT CAA TTA TTT AAA GAA GGC ATA CGA    2252
Trp Lys His Ser Ile Lys Asn Asn Gln Leu Phe Lys Glu Gly Ile Arg
            205                 210                 215

AAC TAT TCA GAA ATA TCT TCA TTA CCC TAT GAA GAA GAT CAT AAT TTT    2300
Asn Tyr Ser Glu Ile Ser Ser Leu Pro Tyr Glu Glu Asp His Asn Phe
            220                 225                 230

GAT ATT GAT TTA GTA TTT ACT TGG GTC AAC TCA GAA GAT AAG AAT TGG    2348
Asp Ile Asp Leu Val Phe Thr Trp Val Asn Ser Glu Asp Lys Asn Trp
235                 240                 245                 250

CAA GAG TTA TAT AAA AAA TAT AAG CCC GAC TTT AAT AGC GAT GCA ACC    2396
Gln Glu Leu Tyr Lys Lys Tyr Lys Pro Asp Phe Asn Ser Asp Ala Thr
            255                 260                 265

AGT ACA TCA AGA TTC CTT AGT AGA GAT GAA TTA AAA TTC GCA TTA CGC    2444
Ser Thr Ser Arg Phe Leu Ser Arg Asp Glu Leu Lys Phe Ala Leu Arg
            270                 275                 280

TCT TGG GAA ATG AGT GGA TCC TTC ATT CGA AAA ATT TTT ATT GTC TCT    2492
Ser Trp Glu Met Ser Gly Ser Phe Ile Arg Lys Ile Phe Ile Val Ser
            285                 290                 295

AAT TGT GCT CCC CCA GCA TGG CTA GAT TTA AAT AAC CCT AAA ATT CAA    2540
Asn Cys Ala Pro Pro Ala Trp Leu Asp Leu Asn Asn Pro Lys Ile Gln
300                 305                 310

TGG GTA TAT CAC GAA GAA ATT ATG CCA CAA AGT GCC CTT CCT ACT TTT    2588
Trp Val Tyr His Glu Glu Ile Met Pro Gln Ser Ala Leu Pro Thr Phe
315                 320                 325                 330

AGC TCA CAT GCT ATT GAA ACC AGC TTG CAC CAT ATA CCA GGA ATT AGT    2636
Ser Ser His Ala Ile Glu Thr Ser Leu His His Ile Pro Gly Ile Ser
            335                 340                 345

AAC TAT TTT ATT TAC AGC AAT GAC GAC TTC CTA TTA ACT AAA CCA TTG    2684
Asn Tyr Phe Ile Tyr Ser Asn Asp Asp Phe Leu Leu Thr Lys Pro Leu
            350                 355                 360

AAT AAA GAC AAT TTC TTC TAT TCG AAT GGT ATT GCA AAG TTA AGA TTA    2732
Asn Lys Asp Asn Phe Phe Tyr Ser Asn Gly Ile Ala Lys Leu Arg Leu
            365                 370                 375

GAA GCA TGG GGA AAT GTT AAT GGT GAA TGT ACT GAA GGA GAA CCT GAC    2780
Glu Ala Trp Gly Asn Val Asn Gly Glu Cys Thr Glu Gly Glu Pro Asp
            380                 385                 390

TAC TTA AAT GGT GCT CGC AAT GCG AAC ACT CTC TTA GAA AAG GAA TTT    2828
Tyr Leu Asn Gly Ala Arg Asn Ala Asn Thr Leu Leu Glu Lys Glu Phe
395                 400                 405                 410

AAA AAA TTT ACT ACT AAA CTA CAT ACT CAC TCC CCT CAA TCC ATG AGA    2876
Lys Lys Phe Thr Thr Lys Leu His Thr His Ser Pro Gln Ser Met Arg
            415                 420                 425

ACT GAT ATT TTA TTT GAG ATG GAA AAA AAA TAT CCA GAA GAG TTT AAT    2924
Thr Asp Ile Leu Phe Glu Met Glu Lys Lys Tyr Pro Glu Glu Phe Asn
            430                 435                 440

AGA ACA CTA CAT AAT AAA TTC CGA TCT TTA GAT GAT ATT GCA GTA ACG    2972
Arg Thr Leu His Asn Lys Phe Arg Ser Leu Asp Asp Ile Ala Val Thr
            445                 450                 455

GGC TAT CTC TAT CAT CAT TAT GCC CTA CTC TCT GGA CGA GCA CTA CAA    3020
Gly Tyr Leu Tyr His His Tyr Ala Leu Leu Ser Gly Arg Ala Leu Gln
460                 465                 470

AGT TCT GAC AAG ACG GAA CTT GTA CAG CAA AAT CAT GAT TTC AAA AAG    3068
Ser Ser Asp Lys Thr Glu Leu Val Gln Gln Asn His Asp Phe Lys Lys
475                 480                 485                 490
```

```
AAA CTA AAT AAT GTA GTG ACC TTA ACT AAA GAA AGG AAT TTT GAC AAA        3116
Lys Leu Asn Asn Val Val Thr Leu Thr Lys Glu Arg Asn Phe Asp Lys
            495                 500                 505

CTT CCT TTG AGC GTA TGT ATC AAC GAT GGT GCT GAT AGT CAC TTG AAT        3164
Leu Pro Leu Ser Val Cys Ile Asn Asp Gly Ala Asp Ser His Leu Asn
            510                 515                 520

GAA GAA TGG AAT GTT CAA GTT ATT AAG TTC TTA GAA ACT CTT TTC CCA        3212
Glu Glu Trp Asn Val Gln Val Ile Lys Phe Leu Glu Thr Leu Phe Pro
            525                 530                 535

TTA CCA TCA TCA TTT GAG AAA TAA GTTAAATTAT GAAGAACCTT TGAGTGCAAT       3266
Leu Pro Ser Ser Phe Glu Lys  *
        540             545

TCGAAGGTTC TTCATTCATA TTATTCATAT TTTGGAGAAA TT ATG TTA TCT AAT         3320
                                              Met Leu Ser Asn
                                                1

TTA AAA ACA GGA AAT AAT ATC TTA GGA TTA CCT GAA TTT GAG TTG AAT        3368
Leu Lys Thr Gly Asn Asn Ile Leu Gly Leu Pro Glu Phe Glu Leu Asn
 5                  10                  15                  20

GGC TGC CGA TTC TTA TAT AAA AAA GGT ATA GAA AAA ACA ATT ATT ACT        3416
Gly Cys Arg Phe Leu Tyr Lys Lys Gly Ile Glu Lys Thr Ile Ile Thr
                25                  30                  35

TTT TCA GCA TTT CCT CCT AAA GAT ATT GCT CAA AAA TAT AAT TAT ATA        3464
Phe Ser Ala Phe Pro Pro Lys Asp Ile Ala Gln Lys Tyr Asn Tyr Ile
            40                  45                  50

AAA GAT TTT TTA AGT TCT AAT TAT ACT TTT TTA GCA TTC TTA GAT ACC        3512
Lys Asp Phe Leu Ser Ser Asn Tyr Thr Phe Leu Ala Phe Leu Asp Thr
        55                  60                  65

AAA TAT CCA GAA GAT GAT GCT AGA GGC ACT TAT TAC ATT ACT AAT GAG        3560
Lys Tyr Pro Glu Asp Asp Ala Arg Gly Thr Tyr Tyr Ile Thr Asn Glu
 70                  75                  80

TTA GAT AAT GGA TAT TTA CAA ACC ATA CAT TGT ATT ATT CAA TTA TTA        3608
Leu Asp Asn Gly Tyr Leu Gln Thr Ile His Cys Ile Ile Gln Leu Leu
 85                  90                  95                  100

TCG AAT ACA AAT CAA GAA GAT ACC TAC CTT TTG GGT TCA AGT AAA GGT        3656
Ser Asn Thr Asn Gln Glu Asp Thr Tyr Leu Leu Gly Ser Ser Lys Gly
                105                 110                 115

GGC GTT GGC GCA CTT CTA CTC GGT CTT ACA TAT AAT TAT CCT AAT ATA        3704
Gly Val Gly Ala Leu Leu Leu Gly Leu Thr Tyr Asn Tyr Pro Asn Ile
            120                 125                 130

ATT ATT AAT GCT CCT CAA GCC AAA TTA GCA GAT TAT ATC AAA ACA CGC        3752
Ile Ile Asn Ala Pro Gln Ala Lys Leu Ala Asp Tyr Ile Lys Thr Arg
        135                 140                 145

TCG AAA ACC ATT CTT TCA TAT ATG CTT GGA ACC TCT AAA AGA TTT CAA        3800
Ser Lys Thr Ile Leu Ser Tyr Met Leu Gly Thr Ser Lys Arg Phe Gln
 150                 155                 160

GAT ATT AAT TAC GAT TAT ATC AAT GAC TTC TTA CTA TCT AAA ATT AAG        3848
Asp Ile Asn Tyr Asp Tyr Ile Asn Asp Phe Leu Leu Ser Lys Ile Lys
 165                 170                 175                 180

ACT TGC GAC TCC TCA CTT AAA TGG AAT ATT CAT ATA ACT TGC GGA AAA        3896
Thr Cys Asp Ser Ser Leu Lys Trp Asn Ile His Ile Thr Cys Gly Lys
                185                 190                 195

GAT GAT TCA TAT CAT TTA AAT GAA TTA GAA ATT CTA AAA AAT GAA TTT        3944
Asp Asp Ser Tyr His Leu Asn Glu Leu Glu Ile Leu Lys Asn Glu Phe
            200                 205                 210

AAT ATA AAA GCT ATT ACG ATT AAA ACC AAA CTA ATT TCT GGC GGG CAT        3992
Asn Ile Lys Ala Ile Thr Ile Lys Thr Lys Leu Ile Ser Gly Gly His
        215                 220                 225

GAT AAT GAA GCA ATT GCC CAC TAT AGA GAA TAC TTT AAA ACC ATA ATC        4040
Asp Asn Glu Ala Ile Ala His Tyr Arg Glu Tyr Phe Lys Thr Ile Ile
```

```
                230              235              240
CAA AAT ATA TAA A ATG CGT AAG ATT ACT TTT ATT ATC CCT ATA AAA    4086
Gln Asn Ile *   Met Arg Lys Ile Thr Phe Ile Ile Pro Ile Lys
245              1               5                       10

CAG TCT TTA ATA AAA CCT GAT TGC TTT ATA CGC CTC TTT TTT AAT TTA  4134
Gln Ser Leu Ile Lys Pro Asp Cys Phe Ile Arg Leu Phe Phe Asn Leu
            15              20                      25

TTT TTG CTA AAA AAA TTC TCA AGT AAA TAC GGA TTT TCT ATA TTA GTT  4182
Phe Leu Leu Lys Lys Phe Ser Ser Lys Tyr Gly Phe Ser Ile Leu Val
        30              35                  40

GCA GAC AAC AGT AAC TTC CTT TGG AAA AAT ATT ATT AAA TTA ATT ACA  4230
Ala Asp Asn Ser Asn Phe Leu Trp Lys Asn Ile Ile Lys Leu Ile Thr
    45              50                  55

AAA TTT TAC AAA TGT AAT TAT ATT AGT ATT AAA TCT CAT AAT ACT TTT  4278
Lys Phe Tyr Lys Cys Asn Tyr Ile Ser Ile Lys Ser His Asn Thr Phe
60              65                  70                      75

TAT ACG CCT GCT AAA ATT AAA AAT GCA GCT GCC ATC TAT AGT TTT AAT  4326
Tyr Thr Pro Ala Lys Ile Lys Asn Ala Ala Ala Ile Tyr Ser Phe Asn
            80              85                      90

ACC TTG AAT TCA AAT TAC ATT TTA TTC TTA GAT GTT GAC GTT TTA TTA  4374
Thr Leu Asn Ser Asn Tyr Ile Leu Phe Leu Asp Val Asp Val Leu Leu
        95              100                 105

TCG GAA AAT TTT ATC CAA CAT TTA ATA AAA AAA ACA AAA ACC AAT ATC  4422
Ser Glu Asn Phe Ile Gln His Leu Ile Lys Lys Thr Lys Thr Asn Ile
    110             115                 120

GCC TTT GAT TGG TAC CCT GTT TCA TTC TTA AAC AAA CAA TTT GGG ATT  4470
Ala Phe Asp Trp Tyr Pro Val Ser Phe Leu Asn Lys Gln Phe Gly Ile
125             130                 135

ATA AAT TTT ATA TTA TTC TCA TAT AAA GGT AAT CTA AAT ATA GAA GAA  4518
Ile Asn Phe Ile Leu Phe Ser Tyr Lys Gly Asn Leu Asn Ile Glu Glu
140             145                 150                 155

TCA TTC ATT ATA CAA ACA GGG TTT GTA ACT GGC TTA CAA TTA TTT AAT  4566
Ser Phe Ile Ile Gln Thr Gly Phe Val Thr Gly Leu Gln Leu Phe Asn
            160                 165                 170

TCT GAT TTT TTC TAC AAA ACA GCT GGA TAC AAT GAA AGC TTT CTT GGC  4614
Ser Asp Phe Phe Tyr Lys Thr Ala Gly Tyr Asn Glu Ser Phe Leu Gly
        175                 180                 185

TAT GGC TGT GAA GAT ATT GAA ATG ATT CAC AGA GCA ACA TTA TTA TTA  4662
Tyr Gly Cys Glu Asp Ile Glu Met Ile His Arg Ala Thr Leu Leu Leu
    190                 195                 200

AAT ATT AGA CCT GCC TTT AAT GAA AAT CAT CAA TAT TTT ACA GAT GAT  4710
Asn Ile Arg Pro Ala Phe Asn Glu Asn His Gln Tyr Phe Thr Asp Asp
205                 210                 215

AGA GGA TAT ATG CCT TCT AAA TTA ACC GGA TTT CGA AAT TAT TTT TAT  4758
Arg Gly Tyr Met Pro Ser Lys Leu Thr Gly Phe Arg Asn Tyr Phe Tyr
220             225                 230                 235

TAT TTG AAA AGA GAT GAA TTT TCA AAC TTA CAG ATA ACT CCT AAA CAT  4806
Tyr Leu Lys Arg Asp Glu Phe Ser Asn Leu Gln Ile Thr Pro Lys His
            240                 245                 250

TTC TGG CAT AAG CGA AAA AAT AAA TCA AAA TAT CTA AAA AAT AGA TAT  4854
Phe Trp His Lys Arg Lys Asn Lys Ser Lys Tyr Leu Lys Asn Arg Tyr
        255                 260                 265

CAA AAT GAT GTA AAA ATG ATT CAG ATT ATG AAA GAT TTT GAT CGA AAA  4902
Gln Asn Asp Val Lys Met Ile Gln Ile Met Lys Asp Phe Asp Arg Lys
    270                 275                 280

TTT CTA AAA AAT TAA CGAGCTGTCT TGCCCATATG AATCCTGATT ACTTTAATTT  4957
Phe Leu Lys Asn *
285

AATTATGAAA AATATTCTCG TTACCGGCGG CACCGGTTTT ATCGGCTCGC ACACCGTTGT  5017
```

```
TTCTTTGCTG AAAAGCGGCC ATCAAGTCGT GATTTTGGAT AACCTAT                              5064
```

(2) INFORMATION FOR SEQ ID NO:9:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:9:

```
Met Lys Val Leu Thr Val Phe Gly Thr Arg Pro Glu Ala Ile Lys Met
 1               5                  10                  15

Ala Pro Val Ile Leu Glu Leu Gln Lys His Asn Thr Ile Thr Ser Lys
                20                  25                  30

Val Cys Ile Thr Ala Gln His Arg Glu Met Leu Asp Gln Val Leu Ser
            35                  40                  45

Leu Phe Glu Ile Lys Ala Asp Tyr Asp Leu Asn Ile Met Lys Pro Asn
        50                  55                  60

Gln Ser Leu Gln Glu Ile Thr Thr Asn Ile Ile Ser Ser Leu Thr Asp
 65                 70                  75                  80

Val Leu Glu Asp Phe Lys Pro Asp Cys Val Leu Ala His Gly Asp Thr
                85                  90                  95

Thr Thr Thr Phe Ala Ala Ser Leu Ala Ala Phe Tyr Gln Lys Ile Pro
            100                 105                 110

Val Gly His Ile Glu Ala Gly Leu Arg Thr Tyr Asn Leu Tyr Ser Pro
        115                 120                 125

Trp Pro Glu Glu Ala Asn Arg Arg Leu Thr Ser Val Leu Ser Gln Trp
130                 135                 140

His Phe Ala Pro Thr Glu Asp Ser Lys Asn Asn Leu Leu Ser Glu Ser
145                 150                 155                 160

Ile Pro Ser Asp Lys Val Ile Val Thr Gly Asn Thr Val Ile Asp Ala
                165                 170                 175

Leu Met Val Ser Leu Glu Lys Leu Lys Ile Thr Thr Ile Lys Lys Gln
            180                 185                 190

Met Glu Gln Ala Phe Pro Phe Ile Gln Asp Asn Ser Lys Val Ile Leu
        195                 200                 205

Ile Thr Ala His Arg Arg Glu Asn His Gly Glu Gly Ile Lys Asn Ile
    210                 215                 220

Gly Leu Ser Ile Leu Glu Leu Ala Lys Lys Tyr Pro Thr Phe Ser Phe
225                 230                 235                 240

Val Ile Pro Leu His Leu Asn Pro Asn Val Arg Lys Pro Ile Gln Asp
                245                 250                 255

Leu Leu Ser Ser Val His Asn Val His Leu Ile Glu Pro Gln Glu Tyr
            260                 265                 270

Leu Pro Phe Val Tyr Leu Met Ser Lys Ser His Ile Ile Leu Ser Asp
        275                 280                 285

Ser Gly Gly Ile Gln Glu Glu Ala Pro Ser Leu Gly Lys Pro Val Leu
    290                 295                 300

Val Leu Arg Asp Thr Thr Glu Arg Pro Glu Ala Val Ala Ala Gly Thr
305                 310                 315                 320

Val Lys Leu Val Gly Ser Glu Thr Gln Asn Ile Ile Glu Ser Phe Thr
                325                 330                 335

Gln Leu Ile Glu Tyr Pro Glu Tyr Tyr Glu Lys Met Ala Asn Ile Glu
```

```
                  340             345              350
Asn Pro Tyr Gly Ile Gly Asn Ala Ser Lys Ile Ile Val Glu Thr Leu
            355             360             365

Leu Lys Asn Arg
        370
```

(2) INFORMATION FOR SEQ ID NO:10:

(i) SEQUENCE CHARACTERISTICS:
        (A) LENGTH: 545 amino acids
        (B) TYPE: amino acid
        (D) TOPOLOGY: linear (ii) MOLECULE TYPE: protein (xi) SEQUENCE DESCRIPTION: SEQ ID NO:10:

```
Met Phe Ile Leu Asn Asn Arg Lys Trp Arg Lys Leu Lys Arg Asp Pro
  1               5                  10                  15

Ser Ala Phe Phe Arg Asp Ser Lys Phe Asn Phe Leu Arg Tyr Phe Ser
                 20                  25                  30

Ala Lys Lys Phe Ala Lys Asn Phe Lys Asn Ser Ser His Ile His Lys
             35                  40                  45

Thr Asn Ile Ser Lys Ala Gln Ser Asn Ile Ser Ser Thr Leu Lys Glu
         50                  55                  60

Asn Arg Lys Gln Asp Met Leu Ile Pro Ile Asn Phe Asn Phe Asn Phe Glu
 65                  70                  75                  80

Tyr Ile Val Lys Lys Leu Asn Asn Gln Asn Ala Ile Gly Val Tyr Ile
                 85                  90                  95

Leu Pro Ser Asn Leu Thr Leu Lys Pro Ala Leu Cys Ile Leu Glu Ser
                100                 105                 110

His Lys Glu Asp Phe Leu Asn Lys Phe Leu Leu Thr Ile Ser Ser Glu
            115                 120                 125

Asn Leu Lys Leu Gln Tyr Lys Phe Asn Gly Gln Ile Lys Asn Pro Lys
130                 135                 140

Ser Val Asn Glu Ile Trp Thr Asp Leu Phe Ser Ile Ala His Val Asp
145                 150                 155                 160

Met Lys Leu Ser Thr Asp Arg Thr Leu Ser Ser Ser Ile Ser Gln Phe
                165                 170                 175

Trp Phe Arg Leu Glu Phe Cys Lys Glu Asp Lys Asp Phe Ile Leu Phe
                180                 185                 190

Ser Thr Ala Asn Arg Tyr Ser Arg Lys Leu Trp Lys His Ser Ile Lys
            195                 200                 205

Asn Asn Gln Leu Phe Lys Glu Gly Ile Arg Asn Tyr Ser Glu Ile Ser
210                 215                 220

Ser Leu Pro Tyr Glu Glu Asp His Asn Phe Asp Ile Asp Leu Val Phe
225                 230                 235                 240

Thr Trp Val Asn Ser Glu Asp Lys Asn Trp Gln Glu Leu Tyr Lys Lys
                245                 250                 255

Tyr Lys Pro Asp Phe Asn Ser Asp Ala Thr Ser Thr Ser Arg Phe Leu
            260                 265                 270

Ser Arg Asp Glu Leu Lys Phe Ala Leu Arg Ser Trp Glu Met Ser Gly
        275                 280                 285

Ser Phe Ile Arg Lys Ile Phe Ile Val Ser Asn Cys Ala Pro Pro Ala
            290                 295                 300

Trp Leu Asp Leu Asn Asn Pro Lys Ile Gln Trp Val Tyr His Glu Glu
305                 310                 315                 320
```

```
Ile Met Pro Gln Ser Ala Leu Pro Thr Phe Ser Ser His Ala Ile Glu
            325                 330                 335

Thr Ser Leu His His Ile Pro Gly Ile Ser Asn Tyr Phe Ile Tyr Ser
            340                 345                 350

Asn Asp Asp Phe Leu Leu Thr Lys Pro Leu Asn Lys Asp Asn Phe Phe
            355                 360                 365

Tyr Ser Asn Gly Ile Ala Lys Leu Arg Leu Glu Ala Trp Gly Asn Val
            370                 375                 380

Asn Gly Glu Cys Thr Glu Gly Glu Pro Asp Tyr Leu Asn Gly Ala Arg
385                 390                 395                 400

Asn Ala Asn Thr Leu Leu Glu Lys Glu Phe Lys Lys Phe Thr Thr Lys
            405                 410                 415

Leu His Thr His Ser Pro Gln Ser Met Arg Thr Asp Ile Leu Phe Glu
            420                 425                 430

Met Glu Lys Lys Tyr Pro Glu Glu Phe Asn Arg Thr Leu His Asn Lys
            435                 440                 445

Phe Arg Ser Leu Asp Asp Ile Ala Val Thr Gly Tyr Leu Tyr His His
            450                 455                 460

Tyr Ala Leu Leu Ser Gly Arg Ala Leu Gln Ser Ser Asp Lys Thr Glu
465                 470                 475                 480

Leu Val Gln Gln Asn His Asp Phe Lys Lys Lys Leu Asn Asn Val Val
            485                 490                 495

Thr Leu Thr Lys Glu Arg Asn Phe Asp Lys Leu Pro Leu Ser Val Cys
            500                 505                 510

Ile Asn Asp Gly Ala Asp Ser His Leu Asn Glu Glu Trp Asn Val Gln
            515                 520                 525

Val Ile Lys Phe Leu Glu Thr Leu Phe Pro Leu Pro Ser Ser Phe Glu
            530                 535                 540

Lys
545

(2) INFORMATION FOR SEQ ID NO:11:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:11:

Met Leu Ser Asn Leu Lys Thr Gly Asn Asn Ile Leu Gly Leu Pro Glu
1               5                   10                  15

Phe Glu Leu Asn Gly Cys Arg Phe Leu Tyr Lys Lys Gly Ile Glu Lys
            20                  25                  30

Thr Ile Ile Thr Phe Ser Ala Phe Pro Pro Lys Asp Ile Ala Gln Lys
            35                  40                  45

Tyr Asn Tyr Ile Lys Asp Phe Leu Ser Ser Asn Tyr Thr Phe Leu Ala
            50                  55                  60

Phe Leu Asp Thr Lys Tyr Pro Glu Asp Asp Ala Arg Gly Thr Tyr Tyr
65                  70                  75                  80

Ile Thr Asn Glu Leu Asp Asn Gly Tyr Leu Gln Thr Ile His Cys Ile
            85                  90                  95

Ile Gln Leu Leu Ser Asn Thr Asn Gln Glu Asp Thr Tyr Leu Leu Gly
            100                 105                 110
```

```
Ser Ser Lys Gly Gly Val Gly Ala Leu Leu Leu Gly Leu Thr Tyr Asn
        115                 120                 125

Tyr Pro Asn Ile Ile Ile Asn Ala Pro Gln Ala Lys Leu Ala Asp Tyr
130                 135                 140

Ile Lys Thr Arg Ser Lys Thr Ile Leu Ser Tyr Met Leu Gly Thr Ser
145                 150                 155                 160

Lys Arg Phe Gln Asp Ile Asn Tyr Asp Tyr Ile Asn Asp Phe Leu Leu
                165                 170                 175

Ser Lys Ile Lys Thr Cys Asp Ser Ser Leu Lys Trp Asn Ile His Ile
            180                 185                 190

Thr Cys Gly Lys Asp Asp Ser Tyr His Leu Asn Glu Leu Glu Ile Leu
        195                 200                 205

Lys Asn Glu Phe Asn Ile Lys Ala Ile Thr Ile Lys Thr Lys Leu Ile
210                 215                 220

Ser Gly Gly His Asp Asn Glu Ala Ile Ala His Tyr Arg Glu Tyr Phe
225                 230                 235                 240

Lys Thr Ile Ile Gln Asn Ile
                245
```

(2) INFORMATION FOR SEQ ID NO:12:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO:12:

```
Met Arg Lys Ile Thr Phe Ile Ile Pro Ile Lys Gln Ser Leu Ile Lys
1               5                   10                  15

Pro Asp Cys Phe Ile Arg Leu Phe Phe Asn Leu Phe Leu Leu Lys Lys
                20                  25                  30

Phe Ser Ser Lys Tyr Gly Phe Ser Ile Leu Val Ala Asp Asn Ser Asn
            35                  40                  45

Phe Leu Trp Lys Asn Ile Ile Lys Leu Ile Thr Lys Phe Tyr Lys Cys
50                  55                  60

Asn Tyr Ile Ser Ile Lys Ser His Asn Thr Phe Tyr Thr Pro Ala Lys
65                  70                  75                  80

Ile Lys Asn Ala Ala Ala Ile Tyr Ser Phe Asn Thr Leu Asn Ser Asn
                85                  90                  95

Tyr Ile Leu Phe Leu Asp Val Asp Val Leu Leu Ser Glu Asn Phe Ile
                100                 105                 110

Gln His Leu Ile Lys Lys Thr Lys Thr Asn Ile Ala Phe Asp Trp Tyr
            115                 120                 125

Pro Val Ser Phe Leu Asn Lys Gln Phe Gly Ile Ile Asn Phe Ile Leu
130                 135                 140

Phe Ser Tyr Lys Gly Asn Leu Asn Ile Glu Glu Ser Phe Ile Ile Gln
145                 150                 155                 160

Thr Gly Phe Val Thr Gly Leu Gln Leu Phe Asn Ser Asp Phe Tyr
                165                 170                 175

Lys Thr Ala Gly Tyr Asn Glu Ser Phe Leu Gly Tyr Gly Cys Glu Asp
            180                 185                 190

Ile Glu Met Ile His Arg Ala Thr Leu Leu Leu Asn Ile Arg Pro Ala
            195                 200                 205

Phe Asn Glu Asn His Gln Tyr Phe Thr Asp Asp Arg Gly Tyr Met Pro
```

```
              210                 215                 220
Ser Lys Leu Thr Gly Phe Arg Asn Tyr Phe Tyr Tyr Leu Lys Arg Asp
225                 230                 235                 240

Glu Phe Ser Asn Leu Gln Ile Thr Pro Lys His Phe Trp His Lys Arg
                245                 250                 255

Lys Asn Lys Ser Lys Tyr Leu Lys Asn Arg Tyr Gln Asn Asp Val Lys
                260                 265                 270

Met Ile Gln Ile Met Lys Asp Phe Asp Arg Lys Phe Leu Lys Asn
        275                 280                 285
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:13:

GTGTGGAAGT TTAATTGTAG GATG                                   24

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:14:

CCACCACCAA ACAATACTGC CG                                     22

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:15:

GCAATACCAT TACGTTTATC TCTC                                   24

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:16:

GTTTCAGGAT TGTTGATTAC TTCAGC                                                26

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:17:

GTCCTACGCC CTGCAGAGCT GG                                                    22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:18:

CATTAGGCCT AAATGCCTGA GG                                                    22

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:19:

GCTGAAGTTG TTAAACATCA AACAC                                                 25

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid

```
        (A) DESCRIPTION: /desc = "Oligonucleotide."

(iii) HYPOTHETICAL: NO (xi) SEQUENCE DESCRIPTION: SEQ ID NO:20:

GCTACGACAG ATGCAAAGGC G                                              21

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:21:

AGAGGATTGG CTATTACATA TAGC                                           24

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (xi) SEQUENCE DESCRIPTION: SEQ ID NO:22:

AGCTCTGTTG TCGATTACTC TCC                                            23

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:23:

CATTACACAG GTTGGCTGGA AGACGG                                         26

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Oligonucleotide."

(iii) HYPOTHETICAL: NO
```

(xi) SEQUENCE DESCRIPTION: SEQ ID NO:24:

GCAGCTCGAC TTCAAATATC AAAGTGGC                                               28

(2) INFORMATION FOR SEQ ID NO:25:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:25:

GCCAGCAGGA AGAAAACCTC G                                                      21

(2) INFORMATION FOR SEQ ID NO:26:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide."

(iii) HYPOTHETICAL: NO (xi) SEQUENCE DESCRIPTION: SEQ ID NO:26:

GCCGTTGTAG CTGTACCACG C                                                      21

(2) INFORMATION FOR SEQ ID NO:27:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide."

(iii) HYPOTHETICAL: NO (iv) ANTI-SENSE: NO (xi) SEQUENCE DESCRIPTION: SEQ ID NO:27:

CACCACCAAA CAATACTGCC                                                        20

(2) INFORMATION FOR SEQ ID NO:28:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide."

(iii) HYPOTHETICAL: NO (xi) SEQUENCE DESCRIPTION: SEQ ID NO:28:

```
GCTTGTTCAT TGCTACCAA GTGG                                                    24
```

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (iv) ANTI-SENSE: NO (xi) SEQUENCE DESCRIPTION: SEQ ID NO:29:

```
CCAGCATCAA TATCCTGCCA CG                                                     22
```

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:30:

```
CCATCATTTG TGCAAGGCTG CG                                                     22
```

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:31:

```
CATCCTACAA TTAAACTTCC ACAC                                                   24
```

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:32:

```
GAATACTAAT TATACTCTAC GTACTC                                                 26
```

(2) INFORMATION FOR SEQ ID NO:33:

```
    (i) SEQUENCE CHARACTERISTICS:
        (A) LENGTH: 275 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:33:

GTCCGGAGAT AACCTATGGG TTAAACGCCC AGGCAATGGA GACTTCAGCG TCAACGAATA      60

TGAAACATTA TTTGGTAAGG TCGCTGCTTG CAATATTCGC AAAGGTGCTC AAATCAAAAA     120

AACTGATATT GAATAAAAAT CTATAAATTG ACTCAATTTA ATGATAATCG GCTGACTTTT     180

CAGTCGATTA TCATTAAAAA TATACGGAAA AACAAATGTT GCAGAAAATA AGAAAAGCTC     240

TCTTCCACCC AAAAAAATTC TTCCAAGATT CCCAG                                275

(2) INFORMATION FOR SEQ ID NO:34:

(i) SEQUENCE CHARACTERISTICS:
        (A) LENGTH: 279 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "Consensus sequence
            generated from comparison of SEQ ID NOs:6, 7 and 29."

(iii) HYPOTHETICAL: YES (ix) FEATURE:
        (A) NAME/KEY: misc_feature
        (B) LOCATION: 191..195
        (D) OTHER INFORMATION: /note= "At positions 191-195, N can
            be A, T, C or G or no nucleotide."

(xi) SEQUENCE DESCRIPTION: SEQ ID NO:34:

GTCCGGAGAT AACCTATGGG TTAAACGCCC AGGCAATGGA GACTTCAGCG TCAACGAATA      60

TGAAACATTA TTTGGTAAGG TCGCTGCTTG CAATATTCGC AAAGGTGCTC AAATCAAAAA     120

AACTGATATT GAATAANNNT NTATNAANTA NTNANTTTAN TNANANNNGN NTGNCTNTTN     180

NNNNNAGNNN ATTNTCATTA ANNNTNNANN GANANANNAA TGNTNNAGAA AATAANAAAA     240

GCTCTNTTNC ANCCNAAAAA NTTNTTNCAA GATTCNNNG                            279

(2) INFORMATION FOR SEQ ID NO:35:

(i) SEQUENCE CHARACTERISTICS:
        (A) LENGTH: 410 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:35:

TGAGACAACT TTTTTTGCAC TTGGGCCAGA GGAGGGAATA GCACTACATA GCACTACATG      60

CACTTCCCAA AATTAAAAAA GAAATTACAA TACAAAACTT TAACTTAAGC ATAAAATAAA     120

AAATCTCATT AAGTATGATT GTTTTTAAAT AAATTTAAAA CCTACCAGAG ATACAATACC     180

ACTTTATTTT GTAGAACACA AACGTGTATA ATATATGACA TAAACATCAT CTTCGAAATA     240

ATATTGGGGC TTAGGAAGCA AAATCATCAA AAAACGTGAT AAGCTCCTAA TATTTTTAAC     300
```

```
ACATTACTAT ATTACACATA GGATATTCCA ATGAAAGTCT TAACCGTCTT TGGCACTCGC      360

CCTGAAGCTA TTAAAATGGC GCCTGTAATT CTAGAGTTAC AAAAACATAA                 410
```

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:36:

```
CCACCACCAA ACAATACTGC CG                                               22
```

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:37:

```
GTCAACTCAG AAGATAAGAA TTGG                                             24
```

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:38:

```
TCTCTTTTGT GATTCCGCTC C                                                21
```

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:39:

```
GAATAGCACT ACATGCACTT CCC                                              23
```

(2) INFORMATION FOR SEQ ID NO:40:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:40:

CAGGGCGAGT GCCAAAGACG                                              20

(2) INFORMATION FOR SEQ ID NO:41:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:41:

GAAGCTGTAG CTGCAGGAAC TG                                           22

(2) INFORMATION FOR SEQ ID NO:42:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:42:

AATCATTTCA ATATCTTCAC AGCC                                         24

(2) INFORMATION FOR SEQ ID NO:43:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:43:

TTACCTGAAT TTGAGTTGAA TGGC                                         24

(2) INFORMATION FOR SEQ ID NO:44:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:44:

GTACCAATCA AAGGCGATAT TGG                                              23

(2) INFORMATION FOR SEQ ID NO:45:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:45:

CAAAGGAAGT TACTGTTGTC TGC                                              23

(2) INFORMATION FOR SEQ ID NO:46:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:46:

TTCATATAAC TTGCGGAAAA GATG                                             24

(2) INFORMATION FOR SEQ ID NO:47:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:47:

GAGCCTATTC GAAATCAAAG CTG                                              23

(2) INFORMATION FOR SEQ ID NO:48:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Oligonucleotide."

(iii) HYPOTHETICAL: NO (xi) SEQUENCE DESCRIPTION: SEQ ID NO:48:

-continued

```
AGATACCATT AGTGCATCTA TGAC                                              24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:49:

CATGAAACTC AGCACAGATA GAAC                                              24

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:50:

GTTATTTAAA TCTAGCCATG TGG                                               23

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:51:

CGTGGCAGGA TATTGATGCT GG                                                22
```

We claim:

1. A DNA construct wherein said DNA construct comprises a nucleotide sequence selected from the group consisting of SEQ ID NO:2, SEQ ID NO:3, SEQ ID NO:4, SEQ ID NO:8 (nucleotides 479–1597), SEQ ID NO:8 (nucleotides 1599–3236), SEQ ID NO:8 (nucleotides 3309–4052) and SEQ ID NO:8 (nucleotides 4054–4917), and wherein said DNA construct is not a chromosomal or genomic DNA molecule.

2. A purified DNA preparation comprising at least one serogroup A Neisseria meningitidis strain F8229 coding sequence selected from the group consisting of SEQ ID NO:8 (nucleotides 479–1597; ORF1); SEQ ID NO:8 (nucleotides 1599–3236; ORF2); SEQ ID NO:8 (nucleotides 3309–4052; ORF3); and SEQ ID NO:8 (nucleotides 4054–4917; ORF4), wherein said DNA preparation is not a chromosomal or genomic DNA molecule.

3. The DNA preparation of claim 2 wherein said DNA comprises SEQ ID NO:8 (nucleotides 479–1597; ORF1); SEQ ID NO:8 (nucleotides 1599–3236; ORF2); SEQ ID NO:8 (nucleotides 3309–4052; ORF3); and SEQ ID NO:8 (nucleotides 4054–4917; ORF4) as a biosynthesis genetic cassette determining serogroup specificity.

4. A method of serogroup typing or screening of a particular serogroup marker in a sample comprising a strain of *Neisseria meningitidis,* said method comprising the steps of:

(a) contacting a sample comprising a DNA of a strain of *Neisseria meningitidis* with a detectable nucleic acid molecule selected from the group consisting of SEQ ID NO:2; SEQ ID NO:3; SEQ ID NO:4; at least 20 contiguous nucleotides of SEQ ID NO:8, nucleotides 497–1597; at least 14 contiguous nucleotides of SEQ ID NO:8, nucleotides 1599–3236; at least 14 contiguous nucleotides of SEQ ID NO:8, nucleotides 3309–4052; and at least 14 contiguous nucleotides of SEQ ID NO:8, nucleotides 4054–4917 under stringent hybridization conditions which comprise hybridization at high temperatures (65–68 C. in aqueous solutions and 42 C. in 50% formamide) combined with washing at high temperatures and at low salt concentrations (0.1×SSC);

(b) detecting hybridization of the detectable nucleic acid molecule to the DNA of a strain of *Neisseria meningitidis*, whereby the presence of a particular serogroup marker is detected in the sample by hybridization of said nucleic acid molecule to sample *Neisseria meningitidis* DNA.

5. The method of claim 4, wherein said strain of *Neisseria meningitidis* has at least one capsule switching mutation.

6. A kit useful in detection of a strain of *Neisseria meningitidis* of a particular serogroup, said kit comprising a nucleic acid molecule from the group consisting of SEQ ID NO:2; SEQ ID NO:3; SEQ ID NO:4; at least 20 contiguous nucleotides of SEQ ID NO:8, nucleotides 497–1597; at least 14 contiguous nucleotides of SEQ ID NO:8, nucleotides 1599–3236; at least 14 contiguous nucleotides of SEQ ID NO:8, nucleotides 3309–4052; and at least 14 contiguous nucleotides of SEQ ID NO:8, nucleotides 4054–4917, wherein said nucleic acid molecule anneals to a gene specifying said serogroup, and wherein said nucleic acid molecule is not a chromosomal or genomic DNA molecule.

7. The kit of claim 6 wherein said strain comprises at least one capsule switching mutation.

* * * * *

UNITED STATES PATENT AND TRADEMARK OFFICE
CERTIFICATE OF CORRECTION

PATENT NO. : 6,403,306 B1
DATED : June 11, 2002
INVENTOR(S) : Stephens et al.

It is certified that error appears in the above-identified patent and that said Letters Patent is hereby corrected as shown below:

Column 3,
Line 51, please replace "stains" with -- strains --.

Column 4,
Line 14, please delete "are provided".
Line 48, please replace "with" with -- without --.
Line 66, please replace "cps" with -- *cps* --.

Column 5,
Line 1, please replace "(snyX-D)" with -- (*synX-D*) --.

Column 6,
Line 29, please replace "(C) GA1002" with -- (C), NMB (B), GA 1002 --.
Line 51, please replace "[SEQ ID NO:12]" with -- [SEQ ID NO:11] --.
Line 59, please replace "amino acid protein." with -- amino acid protein [SEQ ID NO:12]. --.

Column 9,
Line 38, please replace "synd" with -- synD --.
Line 48, please replace "sync" with -- synC --.

Column 10,
Line 11, please replace "Cla1" with -- ClaI --.

Column 12,
Line 63, please replace "FIGS. 4A-4B," with -- FIGS. 4A-4B], --.

Column 13,
In Table 2, please replace the nucleotide sequence for primer SE35 "TCTCTTITGTGATTCCGCTCC" with -- TCTCTTTTGTGATTCCGCTCC --.
In Table 2, please replace the nucleotide sequence for primer SE57 "TTACCTGAATFTGAGTTGAATGGC" with
-- TTACCTGAATTTGAGTTGAATGGC --.
In Table 2, please replace the nucleotide sequence for primer JS105 "GTTATFTAAATCTAGCCATGTGG" with -- GTTATTTAAATCTAGCCATGTGG --.
Line 66, please delete "putative".

Column 14,
Line 35, please replace "etrA-D" with -- ctrA-D --.

Column 16,
Line 37, please replace "Neissetia" with -- Neisseria --.

UNITED STATES PATENT AND TRADEMARK OFFICE
CERTIFICATE OF CORRECTION

PATENT NO.    : 6,403,306 B1
DATED         : June 11, 2002
INVENTOR(S)   : Stephens et al.

It is certified that error appears in the above-identified patent and that said Letters Patent is hereby corrected as shown below:

Column 21,
Line 6, please replace "fluorescentagents" with -- fluorescent agents --.

Column 24,
Line 31, please replace "F8229OF2Ω" with -- F8229ORF2Ω --.
Line 58, please replace "an" with -- and --.

Column 25,
Line 63, please replace "produce" with -- product --.

Column 26,
Line 29, please replace "Na$_2$HPO$_4$. 7H$_2$O" with -- Na$_2$HPO$_4$·7H$_2$O --.
Line 32, please replace "M MgSO$_4$. 7H$_2$O" with -- M MgSO$_4$ · 7H$_2$O --.

Column 27,
Line 13, please replace "ID NO:151]" with -- ID NO:15] --.

Column 29,
Line 26, please replace "anΩ-spectinomycin" with -- an Ω-spectinomycin --.

Column 30,
Line 45, please replace "aide" with -- azide --.
Line 45, please replace "56 for 30 minutes" with -- 56°C for 30 minutes --.

Column 75,
Line 4, please insert -- (5-25C below T$_m$) -- after "at high temperatures".

Signed and Sealed this

First Day of July, 2003

JAMES E. ROGAN
*Director of the United States Patent and Trademark Office*